United States Patent
Eriksen et al.

(10) Patent No.: US 8,362,024 B2
(45) Date of Patent: Jan. 29, 2013

(54) PURINYL DERIVATIVES AND THEIR USE AS POTASSIUM CHANNEL MODULATORS

(75) Inventors: Birgitte L. Eriksen, Farum (DK); Ulrik Svane Sørensen, Søborg (DK); Charlotte Hougaard, Bagsværd (DK); Dan Peters, Malmö (SE); Tina Holm Johansen, Smørum (DK); Palle Christophersen, Ballerup (DK)

(73) Assignee: NeuroSearch A/S, Ballerup (DK)

( * ) Notice: Subject to any disclaimer, the term of this patent is extended or adjusted under 35 U.S.C. 154(b) by 467 days.

(21) Appl. No.: 12/593,194

(22) PCT Filed: Mar. 27, 2008

(86) PCT No.: PCT/EP2008/053648
§ 371 (c)(1),
(2), (4) Date: Jan. 29, 2010

(87) PCT Pub. No.: WO2008/116909
PCT Pub. Date: Oct. 2, 2008

(65) Prior Publication Data
US 2010/0120797 A1 May 13, 2010

Related U.S. Application Data

(60) Provisional application No. 60/908,503, filed on Mar. 28, 2007.

(30) Foreign Application Priority Data

Mar. 28, 2007 (DK) ................. 2007 00482

(51) Int. Cl.
C07D 473/16 (2006.01)
A61K 31/52 (2006.01)
C07D 473/40 (2006.01)

(52) U.S. Cl. ............ 514/263.2; 544/264; 544/277; 546/309; 549/439; 564/218; 564/309

(58) Field of Classification Search .......... 544/277; 514/263.2, 263.23
See application file for complete search history.

(56) References Cited

U.S. PATENT DOCUMENTS

| | | | |
|---|---|---|---|
| 6,743,798 B1 * | 6/2004 | Straub et al. ........... | 514/263.2 |
| 7,091,346 B1 | 8/2006 | Zimmermann et al. | |
| 7,176,312 B2 | 2/2007 | Ding et al. | |
| 2002/0068721 A1 | 6/2002 | Weigele et al. | |
| 2003/0139427 A1 | 7/2003 | Castelhano et al. | |
| 2003/0229105 A1 | 12/2003 | Kashanchi | |
| 2004/0116376 A1 | 6/2004 | Elzein et al. | |
| 2005/0124637 A1 * | 6/2005 | Cheng et al. ........... | 514/263.2 |
| 2005/0165029 A1 | 7/2005 | Patel et al. | |
| 2005/0187389 A1 | 8/2005 | Milanov et al. | |
| 2005/0288503 A1 | 12/2005 | Adams et al. | |
| 2006/0009642 A1 | 1/2006 | Ding et al. | |
| 2007/0249639 A1 | 10/2007 | Baenteli et al. | |
| 2007/0275986 A1 | 11/2007 | Becq et al. | |
| 2008/0242683 A1 | 10/2008 | Fairhurst et al. | |
| 2008/0275045 A1 | 11/2008 | Eriksen et al. | |
| 2009/0030019 A1 | 1/2009 | Meijer et al. | |
| 2009/0036475 A1 | 2/2009 | Eriksen et al. | |
| 2009/0306102 A1 | 12/2009 | Eriksen et al. | |
| 2010/0035934 A1 | 2/2010 | Eriksen et al. | |
| 2010/0056494 A1 * | 3/2010 | Winzeler et al. ........... | 514/263.2 |
| 2010/0105705 A1 | 4/2010 | Eriksen et al. | |
| 2010/0130516 A1 * | 5/2010 | Eriksen et al. ........... | 514/263.2 |
| 2010/0152210 A1 | 6/2010 | Eriksen et al. | |
| 2010/0183564 A1 * | 7/2010 | Boitano et al. ........... | 514/263.2 |

(Continued)

FOREIGN PATENT DOCUMENTS

EP 1 724 268 A1 11/2006
WO WO-97/16452 A1 5/1997

(Continued)

OTHER PUBLICATIONS

Brown et al., "Heterocyclic Amplifiers of Phleomycin. VI Some Phenylpurines, Phenylpteridines, Phenylquinazolines and Related Compounds", Australian Journal of Chemistry, vol. 38, pp. 467-474, XP009034595 Jan. 1, 1985.

(Continued)

Primary Examiner — Mark Berch
(74) Attorney, Agent, or Firm — Bird, Stewart, Kolasch & Birch, LLP

(57) ABSTRACT

This invention relates to novel purinyl derivatives of formula Ia or Ib

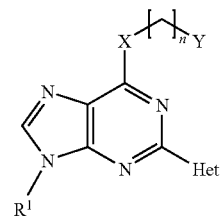
(Ia)

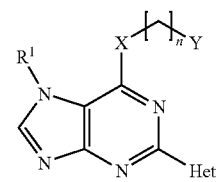

(Ib)

Wherein the symbols are as defined in the Specification and of pharmaceutically acceptable salts thereof useful for the treatment or alleviation of diseases or disorders associated with the activity of potassium channels, for the preparation of a medicament for such treatment and to pharmaceutical compositions containing such compounds.

7 Claims, No Drawings

U.S. PATENT DOCUMENTS

| | | | |
|---|---|---|---|
| 2010/0197914 A1* | 8/2010 | Fairhurst | 544/277 |
| 2011/0144140 A1 | 6/2011 | Eriksen et al. | |
| 2011/0237607 A1* | 9/2011 | Eriksen et al. | 514/263.2 |
| 2011/0251217 A1* | 10/2011 | Eriksen et al. | 514/263.2 |
| 2012/0004246 A1* | 1/2012 | Eriksen et al. | 514/263.2 |

FOREIGN PATENT DOCUMENTS

| | | |
|---|---|---|
| WO | WO-97/20842 A1 | 6/1997 |
| WO | WO-01/44259 A1 | 6/2001 |
| WO | WO-01/44260 A2 | 6/2001 |
| WO | WO-03/002565 A1 | 1/2003 |
| WO | WO-03/014137 A1 | 2/2003 |
| WO | WO-03/031406 A2 | 4/2003 |
| WO | WO-2004/021979 A2 | 3/2004 |
| WO | WO-2005/080377 A1 | 9/2005 |
| WO | WO-2006/074925 A1 | 7/2006 |
| WO | WO-2006/097260 A1 | 9/2006 |
| WO | WO-2006/125211 A1 | 11/2006 |
| WO | WO-2008/040753 A1 | 4/2008 |

OTHER PUBLICATIONS

Jacobs et al., "Substituted 2,4-Diaminoquinazolines and 2,4-Diamino-8-Alkylpurines as Antagonists of the Neurokinin-2 ($NK_2$) Receptor", Bioorganic & Medicinal Chemistry Letters, vol. 5, No. 23, pp. 2879-2884, Dec. 7, 1995.

* cited by examiner

PURINYL DERIVATIVES AND THEIR USE AS POTASSIUM CHANNEL MODULATORS

This application is the National Phase of PCT/EP2008/053658 filed on Mar. 27, 2008, which claims priority under 35 U.S.C. 119(e) to U.S. Provisional Application No. 60/908,503 filed on Mar. 28, 2007, and under 35 U.S.C. 119(a) to Patent Application No. PA 2007 00482 filed in Denmark on Mar. 28, 2007, all of which are hereby expressly incorporated by reference into the present application.

TECHNICAL FIELD

This invention relates to novel purinyl derivatives and their use as potassium channel modulating agents. Moreover the invention is directed to pharmaceutical compositions useful for the treatment or alleviation of diseases or disorders associated with the activity of potassium channels.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

SK channels are present in many central neurons and ganglia, where their primary function is to hyperpolarize nerve cells following one or several action potentials, in order to prevent long trains of epileptogenic activity to occur. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia, suggest a role in the pathogenesis of the disease.

Studies indicate that $K^+$ channels may be a therapeutic target in the treatment of a number of diseases including asthma, cystic fibrosis, chronic obstructive pulmonary disease and rhinorrhea, convulsions, vascular spasms, coronary artery spasms, renal disorders, polycystic kidney disease, bladder spasms, overactive bladder, urinary incontinence, bladder outflow obstruction, interstitiel cystitis, irritable bowel syndrome, gastrointestinal dysfunction, secretory diarrhoea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjogren's syndrome, migraine, pain, arrhythmia, hypertension, absence seizures, myotonic muscle dystrophia, xerostomi, diabetes type II, hyperinsulinemia, premature labour, baldness, cancer and immune suppression.

SUMMARY OF THE INVENTION

The present invention resides in the provision of novel chemical compounds capable of modulating SK channels, or subtypes of SK channels.

Accordingly, in its first aspect, the invention provides novel purinyl derivative of Formula Ia or Ib

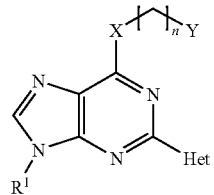

(Ia)

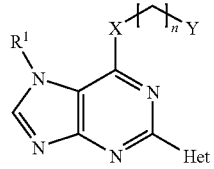

(Ib)

an isomer thereof or a mixture of its isomers, an N-oxide thereof, a prodrug thereof, or a pharmaceutically acceptable salt thereof, wherein n is 0, 1, 2 or 3;

X represents O, S or NR'; wherein R' represents hydrogen, alkyl, cycloalkyl, phenyl or benzyl;

Y represents alkyl, cycloalkyl, phenyl, benzo[1,3]dioxolyl or pyridyl; which alkyl, cycloalkyl, phenyl, benzo[1,3]dioxolyl and pyridyl are optionally substituted with one substituent selected from the group consisting of alkyl, cycloalkyl, halo, trifluoromethyl, trifluoromethoxy, hydroxy, alkoxy, cyano, nitro and amino;

$R^1$ represents hydrogen, alkyl or alkoxy-alkyl; and

Het represents a heterocyclic group selected from pyrazolyl, imidazolyl, indazolyl, benzimidazolyl and pyridinyl, which pyrazolyl, imidazolyl, indazolyl, benzimidazolyl and pyridinyl are substituted two or more times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-di-alkyl-amino-carbonyl, phenyl, benzyl and furanyl.

In another aspect, the invention provides pharmaceutical compositions comprising an effective amount of a compound of the invention.

In further aspects the invention relates to the use of a derivative of the invention for the manufacture of a medicament for the treatment or alleviation of diseases or disorders associated with the activity of potassium channels, and to method of treatment or alleviation of disorders or conditions responsive to modulation of potassium channels.

DETAILED DISCLOSURE OF THE INVENTION

Potassium Channel Modulating Agents

In its first aspect, the invention provides novel purinyl derivatives of Formula Ia or Ib

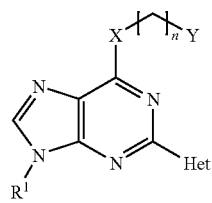
(Ia)

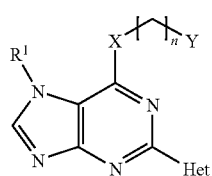
(Ib)

a stereoisomer thereof or a mixture of its stereoisomers, an N-oxide thereof, a prodrug thereof, or a pharmaceutically acceptable salt thereof, wherein n is 0, 1, 2 or 3;

X represents O, S or NR'; wherein R' represents hydrogen, alkyl, cycloalkyl, phenyl or benzyl;

Y represents alkyl, cycloalkyl, phenyl, benzo[1,3]dioxolyl or pyridyl, which alkyl, cycloalkyl, phenyl, benzo[1,3]dioxolyl and pyridyl are optionally substituted with one substituent selected from the group consisting of alkyl, cycloalkyl, halo, trifluoromethyl, trifluoromethoxy, hydroxy, alkoxy, cyano, nitro and amino;

$R^1$ represents hydrogen, alkyl or alkoxy-alkyl; and

Het represents a heterocyclic group selected from pyrazolyl, imidazolyl, indazolyl, benzimidazolyl and pyridinyl, which pyrazolyl, imidazolyl, indazolyl, benzimidazolyl and pyridinyl are substituted two or more times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl, benzyl and furanyl.

In another embodiment the derivative of the invention is a purinyl-pyrazole derivative of Formula IIa or IIb

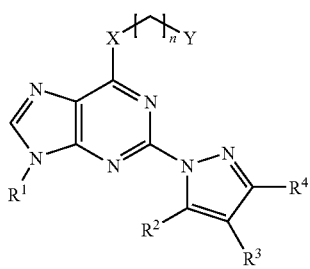
(IIa)

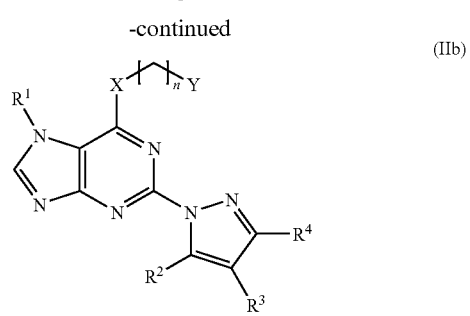

a stereoisomer thereof or a mixture of its stereoisomers, an N-oxide thereof, a prodrug thereof, or a pharmaceutically acceptable salt thereof, wherein n, X, Y and $R^1$ are as defined above; and one of $R^2$, $R^3$ and $R^4$ represents hydrogen; and the other two of $R^2$, $R^3$ and $R^4$, independently of each other, represent alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl, benzyl or furanyl.

In another embodiment the derivative of the invention is a purinyl-indazolyl derivative of Formula IIIa or IIIb (IIIa)

(IIIb)

a stereoisomer thereof or a mixture of its stereoisomers, an N-oxide thereof, a prodrug thereof, or a pharmaceutically acceptable salt thereof, wherein n, X, Y, $R^1$, $R^2$, $R^3$ and $R^4$ are as defined above.

In another embodiment the derivative of the invention is a purinyl-indazolyl derivative of Formula IVa or IVb

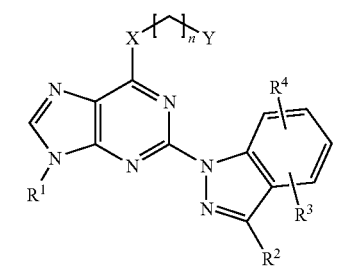
(IVa)

-continued

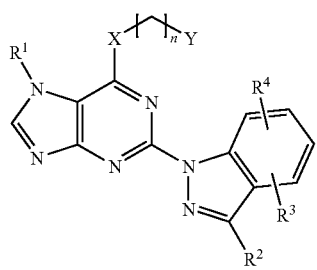
(IVb)

a stereoisomer thereof or a mixture of its stereoisomers, an N-oxide thereof, a prodrug thereof, or a pharmaceutically acceptable salt thereof, wherein n, X, Y, $R^1$, $R^2$, $R^3$ and $R^4$ are as defined above.

In another embodiment the derivative of the invention is a purinyl-benzimidazolyl derivative of Formula Va or Vb

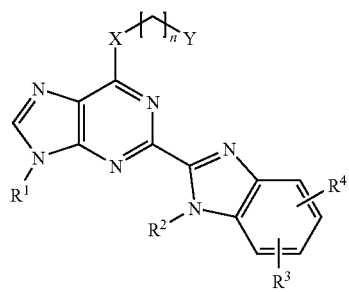
(Va)

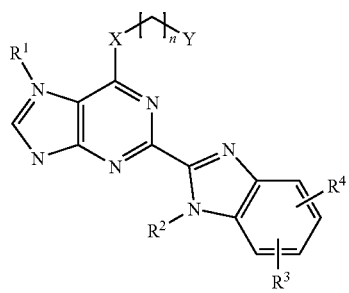
(Vb)

a stereoisomer thereof or a mixture of its stereoisomers, an N-oxide thereof, a prodrug thereof, or a pharmaceutically acceptable salt thereof, wherein n, X, Y, $R^1$, $R^2$, $R^3$ and $R^4$ are as defined above.

In another embodiment the derivative of the invention is a purinyl-pyridinyl derivative of Formula VIa or VIb

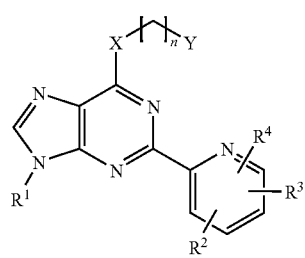
(VIa)

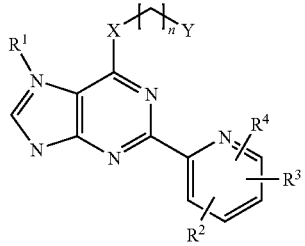
(VIb)

a stereoisomer thereof or a mixture of its stereoisomers, an N-oxide thereof, a prodrug thereof, or a pharmaceutically acceptable salt thereof, wherein n, X, Y, $R^1$, $R^2$, $R^3$ and $R^4$ are as defined above.

In another embodiment the derivative of the invention is a compound of Formula Ia.

In another embodiment the derivative of the invention is a compound of Formula Ib.

In another embodiment the derivative of the invention is a compound of Formula IIa.

In another embodiment the derivative of the invention is a compound of Formula IIb.

In another embodiment the derivative of the invention is a compound of Formula Ia, Ib, IIa, IIb, IIIa, IIIb, IVa, IVb, Va, Vb, VIa or VIb, wherein n is 0, 1, 2 or 3.

In another embodiment n is 0, 1 or 2.

In another embodiment n is 0 or 1.

In another embodiment n is 0.

In another embodiment n is 1.

In another embodiment n is 2.

In another embodiment the derivative of the invention is a compound of formula Ia, Ib, IIa, IIb, IIIa, IIIb, IVa, IVb, Va, Vb, VIa or VIb, wherein X represents O, S or NR'; wherein R' represents hydrogen, alkyl, cycloalkyl, phenyl or benzyl.

In another embodiment X represents NR'; wherein R' represents hydrogen, alkyl or cycloalkyl.

In another embodiment X represents NR'; wherein R' represents hydrogen or methyl.

In another embodiment X represents O, S or NH.

In another embodiment X represents O.

In another embodiment X represents S.

In another embodiment X represents NH.

In another embodiment the derivative of the invention is a compound of Formula Ia, Ib, IIa, IIb, IIIa, IIIb, IVa, IVb, Va, Vb, VIa or VIb, wherein Y represents alkyl, cycloalkyl, phenyl, benzo[1,3]dioxolyl or pyridyl; which alkyl, cycloalkyl, phenyl, benzo[1,3]dioxolyl and pyridyl are optionally substituted with one substituent selected from the group consisting of alkyl, cycloalkyl, halo, trifluoromethyl, trifluoromethoxy, hydroxy, alkoxy, cyano, nitro and amino.

In another embodiment Y represents cycloalkyl, phenyl, benzo[1,3]dioxolyl or pyridyl; which phenyl and pyridyl are optionally substituted with one substituent selected from the group consisting of alkyl, cycloalkyl, halo, trifluoromethyl, trifluoromethoxy, hydroxy, alkoxy, cyano, nitro and amino.

In another embodiment Y represents cycloalkyl, phenyl, benzo[1,3]dioxolyl or pyridyl; which phenyl and pyridyl are optionally substituted with one substituent selected from the group consisting of halo, in particular fluoro or chloro, and trifluoromethyl.

In another embodiment Y represents cycloalkyl, phenyl, benzo[1,3]dioxolyl or pyridyl; which phenyl and pyridyl are optionally substituted with one halo, in particular fluoro, chloro or bromo.

In another embodiment Y represents cycloalkyl, phenyl, benzo[1,3]dioxolyl or pyridyl.

In another embodiment Y represents cycloalkyl, e.g. cyclopropyl, cyclobutyl, cyclopentyl, cyclohexyl or cycloheptyl.

In another embodiment Y represents cyclohexyl.

In another embodiment Y represents benzo[1,3]dioxolyl.

In another embodiment Y represents pyridyl; which pyridyl is optionally substituted with one substituent selected from the group consisting of halo, trifluoromethyl, trifluoromethoxy cyano, nitro and amino.

In another embodiment Y represents pyridyl; which pyridyl is optionally substituted with halo, in particular fluoro, chloro or bromo.

In another embodiment Y represents pyridyl; which pyridyl is optionally substituted with chloro. In another embodiment Y represents pyridyl.

In another embodiment Y represents phenyl; which phenyl is optionally substituted with one substituent selected from the group consisting of halo, trifluoromethyl, trifluoromethoxy cyano, nitro and amino.

In another embodiment Y represents phenyl; which phenyl is optionally substituted with one substituent selected from the group consisting of halo, trifluoromethyl, cyano, nitro and amino.

In another embodiment Y represents phenyl; which phenyl is optionally substituted with halo, in particular fluoro, chloro or bromo.

In another embodiment Y represents phenyl; which phenyl is optionally substituted with fluoro.

In another embodiment Y represents phenyl substituted with fluoro.

In another embodiment Y represents phenyl; which phenyl is optionally substituted with chloro.

In another embodiment Y represents phenyl substituted with chloro.

In another embodiment Y represents phenyl; which phenyl is optionally substituted with trifluoromethyl.

In another embodiment Y represents phenyl substituted with trifluoromethyl.

In another embodiment Y represents phenyl; which phenyl is optionally substituted with cyano.

In another embodiment Y represents phenyl substituted with cyano.

In another embodiment Y represents phenyl; which phenyl is optionally substituted with nitro.

In another embodiment Y represents phenyl substituted with nitro.

In another embodiment Y represents phenyl; which phenyl is optionally substituted with amino.

In another embodiment Y represents phenyl substituted with amino.

In another embodiment Y represents phenyl.

In another embodiment the derivative of the invention is a compound of Formula Ia, Ib, IIa, IIb, IIIa, IIIb, IVa, IVb, Va, Vb, VIa or VIb, wherein $R^1$ represents hydrogen, alkyl or alkoxy-alkyl.

In another embodiment $R^1$ represents hydrogen.

In another embodiment $R^1$ represents alkyl.

In another embodiment $R^1$ represents methyl.

In another embodiment $R^1$ represents ethyl.

In another embodiment $R^1$ represents alkoxy-alkyl.

In another embodiment $R^1$ represents methoxy-ethyl.

In another embodiment $R^1$ represents ethoxy-ethyl.

In another embodiment the derivative of the invention is a compound of formula Ia or Ib, wherein Het represents a heterocyclic group selected from pyrazolyl, imidazolyl, indazolyl, benzimidazolyl and pyridinyl, which pyrazolyl, imidazolyl, indazolyl, benzimidazolyl and pyridinyl are substituted two or more times with substituents selected from the group consisting of alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl, benzyl and furanyl.

In another embodiment the derivative of the invention is a compound of formula Ia or Ib, wherein Het represents a heterocyclic group selected from pyrazolyl and pyridinyl, which pyrazolyl and pyridinyl are substituted two or more times with substituents selected from the group consisting of alkyl, hydroxy-alkyl, halo, trifluoromethyl, alkoxy, alkoxy-carbonyl, nitro, amino, phenyl and furanyl.

In another embodiment the derivative of the invention is a compound of formula Ia or Ib, wherein Het represents a heterocyclic group selected from pyrazolyl and pyridinyl, which pyrazolyl and pyridinyl are substituted two or more times with substituents selected from the group consisting of alkyl, halo, trifluoromethyl, nitro, amino, and phenyl.

In another embodiment the derivative of the invention is a compound of formula Ia or Ib, wherein Het represents a heterocyclic group selected from pyrazolyl and pyridinyl, which pyrazolyl and pyridinyl are substituted two or more times with substituents selected from the group consisting of alkyl, halo and trifluoromethyl.

In another embodiment the derivative of the invention is a compound of formula Ia or Ib, wherein Het represents a heterocyclic group selected from pyrazolyl and pyridinyl, which pyrazolyl and pyridinyl are substituted two or more times with alkyl.

In another embodiment the derivative of the invention is a compound of formula Ia or Ib, wherein Het represents pyrazolyl substituted two or more times with alkyl.

In another embodiment the derivative of the invention is a compound of formula Ia or Ib, wherein Het represents pyrazolyl substituted two times with alkyl.

In another embodiment the derivative of the invention is a compound of formula Ia or Ib, wherein Het represents pyrazolyl substituted two times with methyl.

In another embodiment the derivative of the invention is a compound of formula Ia or Ib, wherein Het represents pyrazolyl substituted three times with alkyl.

In another embodiment the derivative of the invention is a compound of formula Ia or Ib, wherein Het represents pyrazolyl substituted three times with methyl.

In another embodiment the derivative of the invention is a compound of formula Ia or Ib, wherein Het represents pyrazolyl substituted two or more times with halo.

In another embodiment the derivative of the invention is a compound of formula Ia or Ib, wherein Het represents pyrazolyl substituted two or more times with trifluoromethyl.

In another embodiment the derivative of the invention is a compound of formula Ia or Ib, wherein Het represents pyrazolyl substituted two or more times with nitro.

In another embodiment the derivative of the invention is a compound of formula Ia or Ib, wherein Het represents pyrazolyl substituted two or more times with amino.

In another embodiment the derivative of the invention is a compound of formula Ia or Ib, wherein Het represents pyrazolyl substituted two or more times with substituents selected from the group consisting of alkyl and halo.

In another embodiment the derivative of the invention is a compound of formula Ia or Ib, wherein Het represents pyrazolyl substituted two times with substituents selected from the group consisting of alkyl and halo.

In another embodiment the derivative of the invention is a compound of formula Ia or Ib, wherein Het represents pyrazolyl substituted three with substituents selected from the group consisting of alkyl and halo.

In another embodiment the derivative of the invention is a compound of formula Ia or Ib, wherein Het represents pyrazolyl substituted two times with substituents selected from the group consisting of alkyl and trifluoromethyl.

In another embodiment the derivative of the invention is a compound of formula Ia or Ib, wherein Het represents pyrazolyl substituted two times with substituents selected from the group consisting of alkyl and hydroxy-alkyl.

In another embodiment the derivative of the invention is a compound of formula Ia or Ib, wherein Het represents pyrazolyl substituted two times with substituents selected from the group consisting of alkyl and alkoxy-carbonyl.

In another embodiment the derivative of the invention is a compound of formula Ia or Ib, wherein Het represents pyrazolyl substituted two times with substituents selected from the group consisting of alkyl and phenyl.

In another embodiment the derivative of the invention is a compound of formula Ia or Ib, wherein Het represents pyrazolyl substituted two times with substituents selected from the group consisting of alkyl and furanyl.

In another embodiment the derivative of the invention is a compound of Formula IIa, IIb, IIIa, IIIb, IVa, IVb, Va, Vb, VIa or VIb, wherein one of $R^2$, $R^3$ and $R^4$ represents hydrogen; and the other two of $R^2$, $R^3$ and $R^4$, independently of each other, represent alkyl, hydroxy-alkyl, cycloalkyl, cycloalkyl-alkyl, alkenyl, alkynyl, halo, trifluoromethyl, trifluoromethoxy, hydroxy, alkoxy, alkoxy-carbonyl, carboxy, cyano, nitro, amino, amino-carbonyl, N,N-dialkyl-amino-carbonyl, phenyl, benzyl or furanyl.

In another embodiment one of $R^2$, $R^3$ and $R^4$ represents hydrogen; and the other two of $R^2$, $R^3$ and $R^4$, independently of each other, represent alkyl, hydroxy-alkyl, halo, trifluoromethyl, trifluoromethoxy, alkoxy-carbonyl, nitro, amino, phenyl benzyl or furanyl.

In another embodiment one of $R^2$, $R^3$ and $R^4$ represents hydrogen; and the other two of $R^2$, $R^3$ and $R^4$, independently of each other, represent alkyl, halo, trifluoromethyl, nitro or amino.

In another embodiment one of $R^2$, $R^3$ and $R^4$ represents hydrogen; and the other two of $R^2$, $R^3$ and $R^4$, independently of each other, represent alkyl, phenyl or furanyl.

In another embodiment one of $R^2$, $R^3$ and $R^4$ represents hydrogen; and the other two of $R^2$, $R^3$ and $R^4$, independently of each other, represent alkyl.

In another embodiment one of $R^2$, $R^3$ and $R^4$ represents hydrogen; and the other two of $R^2$, $R^3$ and $R^4$, independently of each other, represent halo.

In another embodiment of the invention alkyl represents methyl.

In another embodiment of the invention alkyl represents ethyl.

In another embodiment of the invention halo represents fluoro.

In another embodiment of the invention halo represents chloro.

In another embodiment the derivative of the invention is:
(4-Chloro-phenyl)-[2-(3,5-dimethyl-pyrazol-1-yl)-9-methyl-9H-purin-6-yl]-amine;
Cyclohexyl-[2-(3,5-dimethyl-pyrazol-1-yl)-7-methyl-7H-purin-6-yl]-amine;
(4-Chloro-phenyl)-[2-(3,5-dimethyl-pyrazol-1-yl)-7-methyl-7H-purin-6-yl]-amine;
(4-Chloro-phenyl)-[2-(3,5-dimethyl-pyrazol-1-yl)-9-ethyl-9H-purin-6-yl]-amine;
Benzo[1,3]dioxol-5-yl-[2-(3,5-dimethyl-pyrazol-1-yl)-9-ethyl-9H-purin-6-yl]-amine;
6-(4-Chloro-phenylsulfanyl)-2-(3,5-dimethyl-pyrazol-1-yl)-9-methyl-9H-purine;
[2-(4-Chloro-3-methyl-pyrazol-1-yl)-9-methyl-9H-purin-6-yl]-(4-chloro-phenyl)-amine;
[2-(5-Chloro-3-methyl-pyrazol-1-yl)-9-methyl-9H-purin-6-yl]-(4-chloro-phenyl)-amine;
Cyclohexyl-[2-(3,5-dimethyl-pyrazol-1-yl)-9H-purin-6-yl]-amine;
[2-(3,5-Dimethyl-pyrazol-1-yl)-9-methyl-9H-purin-6-yl]-(4-fluoro-phenyl)-amine;
(4-Chloro-phenyl)-[2-(3,5-dimethyl-pyrazol-1-yl)-9-isobutyl-9H-purin-6-yl]-amine;
(4-Chloro-phenyl)-[2-(3,5-dimethyl-pyrazol-1-yl)-9-(2-ethoxy-ethyl)-9H-purin-6-yl]-amine;
[2-(3,5-Dimethyl-pyrazol-1-yl)-9-methyl-9H-purin-6-yl]-(4-trifluoromethyl-phenyl)-amine;
[2-(3,5-Dimethyl-pyrazol-1-yl)-9-methyl-9H-purin-6-yl]-pyridin-4-yl-amine;
(5-Chloro-pyridin-2-yl)-[2-(3,5-dimethyl-pyrazol-1-yl)-9-methyl-9H-purin-6-yl]-amine;
(6-Chloro-pyridin-3-yl)-[2-(3,5-dimethyl-pyrazol-1-yl)-9-methyl-9H-purin-6-yl]-amine;
[2-(3,5-Dimethyl-pyrazol-1-yl)-9-methyl-9H-purin-6-yl]-(4-nitro-phenyl)-amine;
[2-(3,5-Dimethyl-pyrazol-1-yl)-9-methyl-9H-purin-6-ylamino]-benzonitrile;
[2-(3,5-Dimethyl-pyrazol-1-yl)-9-methyl-9H-purin-6-yl]-phenyl-amine;
[2-(3,5-Dimethyl-pyrazol-1-yl)-9-methyl-9H-purin-6-yl]-phenethyl-amine;
(4-Bromo-phenyl)-[2-(3,5-dimethyl-pyrazol-1-yl)-9-methyl-9H-purin-6-yl]-amine;
(4-Chloro-phenyl)-[9-methyl-2-(5-methyl-3-trifluoromethyl-pyrazol-1-yl)-9H-purin-6-yl]-amine;
(4-Chloro-phenyl)-[2-(3,5-diethyl-pyrazol-1-yl)-9-methyl-9H-purin-6-yl]-amine;
(4-Chloro-phenyl)-[9-methyl-2-(3,4,5-trimethyl-pyrazol-1-yl)-9H-purin-6-yl]-amine;
[2-(4-Chloro-3,5-dimethyl-pyrazol-1-yl)-9-methyl-9H-purin-6-yl]-(4-chloro-phenyl)-amine;
(4-Chloro-phenyl)-[9-methyl-2-(5-methyl-3-phenyl-pyrazol-1-yl)-9H-purin-6-yl]-amine;
(4-Chloro-phenyl)-[2-(3-furan-2-yl-5-methyl-pyrazol-1-yl)-9-methyl-9H-purin-6-yl]-amine;
1-[6-(4-Chloro-phenylamino)-9-methyl-9H-purin-2-yl]-5-methyl-1H-pyrazole-3-carboxylic acid ethyl ester;
[2-(3,5-Bis-trifluoromethyl-pyrazol-1-yl)-9-methyl-9H-purin-6-yl]-(4-chloro-phenyl)-amine;
N-[2-(3,5-Dimethyl-pyrazol-1-yl)-9-methyl-9H-purin-6-yl]-benzene-1,4-diamine;
{2-[6-(4-Chloro-phenylamino)-9-methyl-9H-purin-2-yl]-5-methyl-2H-pyrazol-3-yl}-methanol;
[2-(3,5-Dimethyl-pyrazol-1-yl)-9H-purin-6-yl]-phenyl-amine;
[2-(3,5-Dimethyl-pyrazol-1-yl)-9-(2-methoxy-ethyl)-9H-purin-6-yl]-phenyl-amine; or
a stereoisomer thereof or a mixture of its stereoisomers, an N-oxide thereof, a prodrug thereof, or a pharmaceutically acceptable salt thereof.

Any combination of two or more of the embodiments described herein is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to eighteen carbon atoms ($C_{1-18}$-alkyl), e.g. from one to six carbon atoms ($C_{1-6}$-alkyl; lower alkyl), including pentyl, isopentyl, neopentyl, tertiary pentyl, hexyl and isohexyl. In another embodiment alkyl represents a $C_{1-4}$-alkyl group, including butyl, isobutyl, secondary butyl, and tertiary butyl. In another embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In another embodiment the alkenyl group of the invention comprises of from two to eight carbon atoms ($C_{2-8}$-alkenyl), e.g. from two to six carbon atoms ($C_{2-6}$-alkenyl), including at least one double bond. In another embodiment the alkenyl group of the invention is ethenyl; 1- or 2-propenyl; 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention an alkynyl group designates a straight or branched carbon chain containing one or more triple bonds, including di-ynes, tri-ynes and poly-ynes. In another embodiment the alkynyl group of the invention comprises of from two to eight carbon atoms ($C_{2-8}$-alkynyl), e.g. from two to six carbon atoms ($C_{2-6}$-alkynyl), including at least one triple bond. In another embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-hexynyl, or 1,3-hexadiynyl or 1,3,5-hexatriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a hydroxy-alkyl group designates an alkyl group as defined above, which hydroxy-alkyl group is substituted with one or more hydroxy groups. Examples of hydroxy-alkyl groups of the invention include 2-hydroxy-ethyl, 3-hydroxy-propyl, 4-hydroxy-butyl, 5-hydroxy-pentyl and 6-hydroxy-hexyl.

In the context of this invention a cycloalkyl group designates a cyclic alkyl group, preferably containing of from three to ten carbon atoms ($C_{3-10}$-cycloalkyl), e.g. from three to eight carbon atoms ($C_{3-8}$-cycloalkyl), including cyclopropyl, cyclobutyl, cyclopentyl, cyclohexyl, cycloheptyl and cyclooctyl; or e.g. from three to six carbon atoms ($C_{3-6}$-cycloalkyl), including cyclopropyl, cyclobutyl, cyclopentyl and cyclohexyl.

In the context of this invention a cycloalkyl-alkyl group designates a cycloalkyl group as defined above, which cycloalkyl group is substituted on an alkyl group as also defined above. Examples of cycloalkyl-alkyl groups of the invention include cyclopropylmethyl and cyclopropylethyl.

In the context of this invention an alkoxy group designates an "alkyl-O—" group, wherein alkyl is as defined above. Examples of alkoxy groups of the invention include methoxy and ethoxy.

In the context of this invention an alkoxy-alkyl group designates an "alkyl-β-alkyl-" group, wherein alkyl is as defined above. Examples of alkoxy-alkyl groups of the invention include methoxy-methyl, methoxy-ethyl, ethoxy-methyl, and ethoxy-ethyl.

In the context of this invention an alkoxy-carbonyl group designates an "alkyl-O—CO—" group, wherein alkyl is as defined above. Examples of alkoxy-carbonyl groups of the invention include the methyl-, ethyl- and propyl-ester group.

In the context of this invention an amino-carbonyl group designates an "amino-CO—" group.

In the context of this invention an N,N-dialkyl-amino-carbonyl group designates a (tertiary) amino-carbonyl group, disubstituted with alkyl groups as defined above.

Isomers

The derivatives of the present invention may exist in different stereoisomeric forms, including enantiomers, diastereomers, as well as geometric isomers (cis-trans isomers). The invention includes all such isomers and any mixtures thereof including racemic mixtures.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystal-lisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Pharmaceutically Acceptable Salts

The derivatives of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulfonate derived from methane sulphonic acid, the ethanesulfonate derived from ethane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a derivative of the invention and its pharmaceutically acceptable acid addition salt.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Examples of "onium salts" include the alkyl-onium salts, the cycloalkyl-onium salts, and the cycloalkylalkyl-onium salts.

The derivative of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The derivatives of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

The derivatives of the invention have been subjected to in vitro experiments and found useful as potassium channel modulating agents. The compounds of the invention are capable of selectively modulating SK1, SK2 and/or SK3 channels.

Therefore, in another aspect, the invention relates to the use of the derivatives of the invention for the manufacture of medicaments, which medicament may be useful for the treatment or alleviation of a disease or a disorder associated with the activity of potassium channels, e.g. SK channels, e.g. SK1, SK2 and/or SK3 channels.

In another embodiment, the disease or a disorder associated with the activity of potassium channels is a respiratory disease, epilepsy, convulsions, seizures, absence seizures, vascular spasms, coronary artery spasms, renal disorders, polycystic kidney disease, bladder spasms, overactive bladder (OAB), urinary incontinence, bladder outflow obstruction, interstitiel cystitis (IC), erectile dysfunction, gastrointestinal dysfunction, secretory diarrhoea, ischaemia, cerebral ischaemia, ischaemic heart disease, angina pectoris, coronary heart disease, autism, ataxia, traumatic brain injury, Parkinson's disease, bipolar disorder, psychosis, schizophrenia, anxiety, depression, mania, mood disorders, dementia, memory and attention deficits, Alzheimer's disease, amyotrophic lateral sclerosis (ALS), dysmenorrhea, narcolepsy, Reynaud's disease, intermittent claudication, Sjogren's syndrome, arrhythmia, hypertension, myotonic muscle dystrophia, spasticity, xerostomi, diabetes type II, hyperinsulinemia, premature labour, baldness, cancer, irritable bowel syndrome (IBS), immune suppression, migraine or pain, e.g. pelvic pain or abdominal pain, or withdrawal symptoms caused by the termination of abuse of chemical substances, in particular opioids, heroin, cocaine and morphine, benzodiazepines and benzodiazepine-like drugs, and alcohol.

In another embodiment the disease or a disorder associated with the activity of potassium channels is a respiratory disease, urinary incontinence, erectile dysfunction, anxiety, epilepsy, psychosis, schizophrenia, amyotrophic lateral sclerosis (ALS) or pain.

In another embodiment the disease or a disorder associated with the activity of potassium channels is a respiratory disease, in particular asthma, cystic fibrosis, chronic obstructive pulmonary disease (COPD) or rhinorrhea.

In another embodiment the disease or a disorder associated with the activity of potassium channels is overactive bladder, e.g. urinary incontinence.

In another embodiment the disease or a disorder associated with the activity of potassium channels is urinary incontinence.

In another embodiment the disease or a disorder associated with the activity of potassium channels is epilepsy, seizures, absence seizures or convulsions.

In another embodiment the disease or a disorder associated with the activity of potassium channels is schizophrenia.

In another embodiment the disease or a disorder associated with the activity of potassium channels is pain.

The compounds tested showed a biological activity determined as described herein in the micromolar and sub-micromolar range, i.e. of from below 1 to above 100 µM e.g. from below 0.1 to about 10 µM.

Pharmaceutical Compositions

In yet another aspect the invention provides novel pharmaceutical compositions comprising a therapeutically effective amount of the derivatives of the invention.

While a derivative of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In another embodiment, the invention provides pharmaceutical compositions comprising the derivative of the invention, or a pharmaceutically acceptable salt or derivative thereof, together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The derivates of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The derivative of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The derivative according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

In one embodiment, the invention provides tablets or capsules for oral administration In another embodiment, the invention provides and liquids for intravenous administration and continuous infusion.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, e.g. from about 1 to about 100 mg, e.g. from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Other ranges are from about 0.1 µg/kg to about 10 mg/kg/day i.v., and from about 1 µg/kg to about 100 mg/kg/day p.o.

Methods of Therapy

In another aspect the invention provides a method for the prevention, treatment or alleviation of a disease or a disorder or a condition of a living animal body, including a human, which disease, disorder or condition is responsive to modulation of potassium channels, in particular SK channels, and which method comprises administering to such a living animal body, including a human, in need thereof a therapeutically-effective amount of a derivative of the invention.

The indications contemplated according to the invention are those stated above.

It is at present contemplated that suitable dosage ranges are 0.1 to 1000 milligrams daily, 10-500 milligrams daily, or 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Other ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

2,6-Dichloro-9-methyl-9H-purine and
2,6-Dichloro-7-methyl-7H-purine

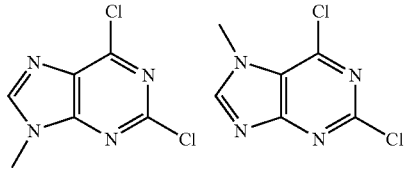

Sodium hydride (60% in mineral oil, 2.53 g, 63.5 mmol) was added to an ice-cooled solution of 2,6-dichloropurine (10.0 g, 52.9 mmol) in tetrahydrofuran (75 mL) and the mixture was stirred for 30 min. Methyl iodide (3.29 mL, 52.9 mmol) was added drop-wise and the reaction mixture was stirred over night. Water was added and the aqueous phase was extracted twice with ethyl acetate. The combined organic phases were dried over magnesium sulphate, filtered and concentrated in vacuo. Dichloromethane was added and undissolved material was collected by filtration. The crystalline compound turned out to be 2,6-dichloro-7-methyl-7H-purine (1.19 g, 11%) The filtrate was concentrated in vacuo and purified by flash chromatography (ethyl acetate/heptane) to give 2,6-dichloro-9-methyl-9H-purine (3.0 g, 28%).

2,6-Dichloro-9-ethyl-9H-purine and
2,6-Dichloro-7-ethyl-7H-purine

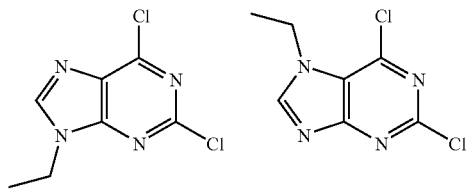

Were prepared according to Example 1 using ethyl iodide instead of methyl iodide.

9-Benzyl-2,6-dichloro-9H-purine and
7-Benzyl-2,6-dichloro-7H-purine

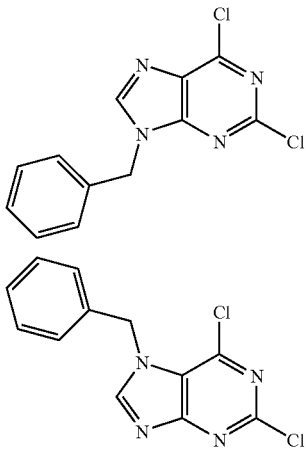

Were prepared according to Example 1 using benzyl bromide instead of methyl iodide.

2,6-Dichloro-9-isobutyl-9H-purine

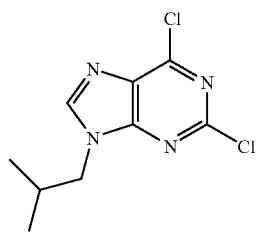

Was prepared according to Example 1 using 1-bromo-2-methylpropane instead of methyl iodide. In this case only one isomer was isolated.

2,6-Dichloro-9-(2-ethoxy-ethyl)-9H-purine

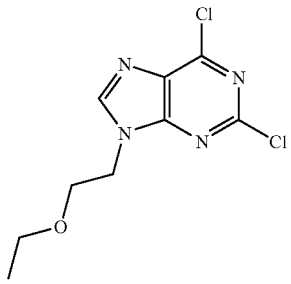 [SMILES: CCOCCn1cnc2c(Cl)nc(Cl)nc21]

Was prepared according to Example 1 using 2-bromoethyl ethylether instead of methyl iodide. In this case only one isomer was isolated.

Example 2

N-(4-Chloro-phenyl)-formamide

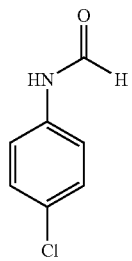

4-Chloroaniline (15 g, 117 mmol) and formic acid (25 mL, 663 mmol) were heated to reflux for 2 hours. The mixture was concentrated in vacuo. Saturated aqueous sodium hydrogen carbonate was added and the aqueous phase was extracted twice with ethyl acetate. The combined organic phases were dried over magnesium sulphate, filtered and concentrated in vacuo to give N-(4-chloro-phenyl)-formamide (17.6 g, 97%) as a grey crystalline compound.

N-Benzo[1,3]dioxol-5-yl-formamide

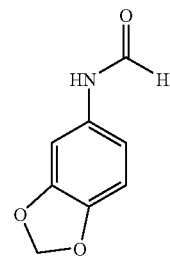 [SMILES: O=CNc1ccc2c(c1)OCO2]

Was prepared according to Example 2 from 3,4-(methylenedioxy)aniline and formic acid.

N-(4-Fluoro-phenyl)-formamide

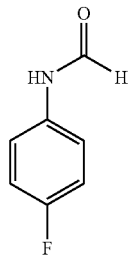

Was prepared according to Example 2 from 4-fluoroaniline and formic acid.

N-(4-Trifluoromethyl-phenyl)-formamide

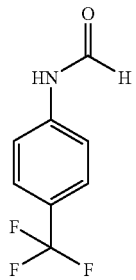

Was prepared according to Example 2 from 4-(trifluoromethyl)aniline and formic acid

N-Pyridin-4-yl-formamide

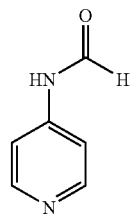

Was prepared according to Example 2 from 4-aminopyridine and formic acid.

N-(5-Chloro-pyridin-2-yl)-formamide

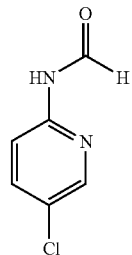

Was prepared according to Example 2 from 2-amino-5-chloropyridine and formic acid.

N-(6-Chloro-pyridin-3-yl)-formamide

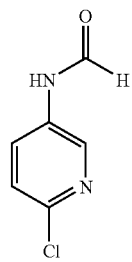

Was prepared according to Example 2 from 5-amino-2-chloropyridine and formic acid.

N-(4-Nitro-phenyl)-formamide

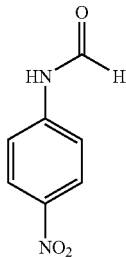

Was prepared according to Example 2 from 4-nitroaniline and formic acid.

N-(4-Cyano-phenyl)-formamide

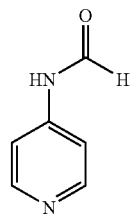

Was prepared according to Example 2 from 4-cyanoaniline and formic acid.

N-Phenyl-formamide

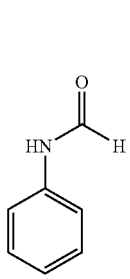

Was prepared according to Example 2 from aniline and formic acid.

N-(4-Bromo-phenyl)-acetamide

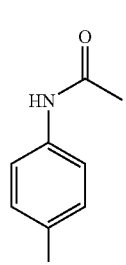

Was prepared according to Example 2 from 4-bromoaniline and formic acid.

Example 3

(2-Chloro-9-methyl-9H-purin-6-yl)-(4-chloro-phenyl)-amine

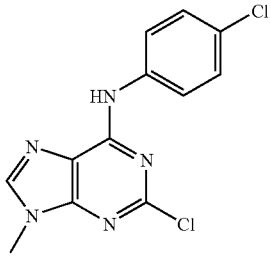 [SMILES: Cn1cnc2c(Nc3ccc(Cl)cc3)nc(Cl)nc21]

N-(4-Chloro-phenyl)-formamide (766 mg, 4.93 mmol) was dissolved in N,N-dimethylformamide (10 mL). Sodium hydride (60% in mineral oil, 240 mg, 5.91 mmol) was added and the mixture was stirred for 30 min. 2,6-Dichloro-9-methyl-9H-purine (1.0 g, 4.93 mmol) was added and the reaction mixture was heated at 80° C. for 2 hours, cooled to room temperature and poured into water. The resulting precipitate was collected by filtration, washed with water and dried to give (2-chloro-9-methyl-9H-purin-6-yl)-(4-chloro-phenyl)-amine (1.2 g, 4.08 mmol, 83%).

(2-Chloro-9-ethyl-9H-purin-6-yl)-(4-chloro-phenyl)-amine

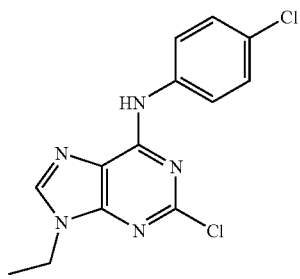 [SMILES: CCn1cnc2c(Nc3ccc(Cl)cc3)nc(Cl)nc21]

Was prepared according to Example 3 from N-(4-chloro-phenyl)-formamide and 2,6-dichloro-9-ethyl-9H-purine.

(2-Chloro-9-isobutyl-9H-purin-6-yl)-(4-chloro-phenyl)-amine

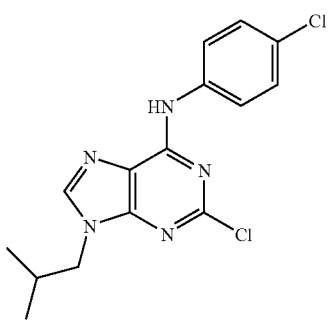 [SMILES: CC(C)Cn1cnc2c(Nc3ccc(Cl)cc3)nc(Cl)nc21]

Was prepared according to Example 3 from N-(4-chloro-phenyl)-formamide and 2,6-dichloro-9-isobutyl-9H-purine.

[2-Chloro-9-(2-ethoxy-ethyl)-9H-purin-6-yl]-(4-chloro-phenyl)-amine

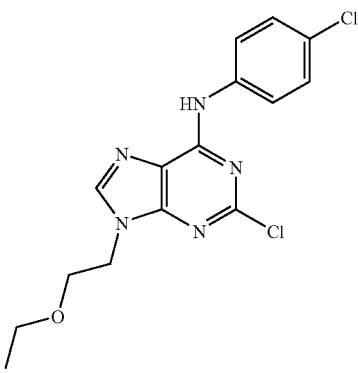 [SMILES: CCOCCn1cnc2c(Nc3ccc(Cl)cc3)nc(Cl)nc21]

Was prepared according to Example 3 from N-(4-chloro-phenyl)-formamide and 2,6-dichloro-9-(2-ethoxy-ethyl)-9H-purine.

(2-Chloro-7-methyl-7H-purin-6-yl)-(4-chloro-phenyl)-amine

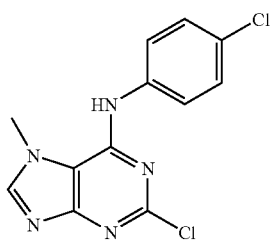 [SMILES: Cn1cnc2nc(Cl)nc(Nc3ccc(Cl)cc3)c21]

Was prepared according to Example 3 from N-(4-chloro-phenyl)-formamide and 2,6-dichloro-7-methyl-7H-purine.

Benzo[1,3]dioxol-5-yl-(2-chloro-9-ethyl-9H-purin-6-yl)-amine

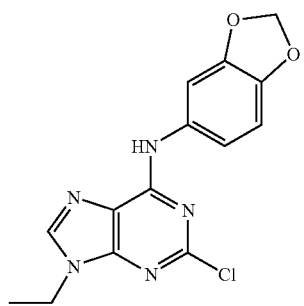 [SMILES: CCn1cnc2c(Nc3ccc4c(c3)OCO4)nc(Cl)nc21]

Was prepared according to Example 3 from N-benzo[1,3]dioxol-5-yl-formamide and 2,6-dichloro-9-ethyl-9H-purine.

25

2-Chloro-6-(4-chloro-phenylsulfanyl)-9-methyl-9H-purine

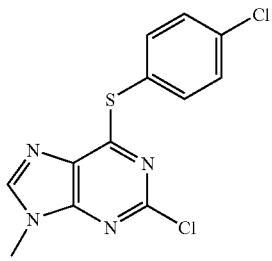 [SMILES: Cn1cnc2c(Sc3ccc(Cl)cc3)nc(Cl)nc21]

Was prepared according to Example 3 from 4-chlorobenzenethiol and 2,6-dichloro-9-ethyl-9H-purine.

(2-Chloro-9-methyl-9H-purin-6-yl)-(4-fluoro-phenyl)-amine

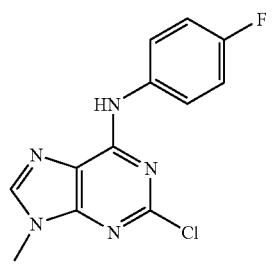 [SMILES: Cn1cnc2c(Nc3ccc(F)cc3)nc(Cl)nc21]

Was prepared according to Example 3 from N-(4-fluoro-phenyl)-formamide and 2,6-dichloro-9-methyl-9H-purine.

(2-Chloro-9-methyl-9H-purin-6-yl)-(4-trifluoromethyl-phenyl)-amine

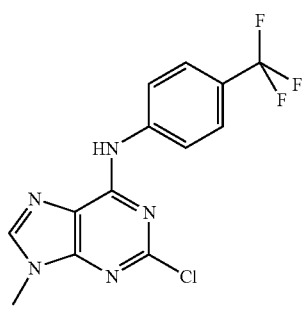 [SMILES: Cn1cnc2c(Nc3ccc(C(F)(F)F)cc3)nc(Cl)nc21]

Was prepared according to Example 3 from N-(4-trifluoromethyl-phenyl)-formamide and 2,6-dichloro-9-methyl-9H-purine.

26

(2-Chloro-9-methyl-9H-purin-6-yl)-pyridin-4-yl-amine

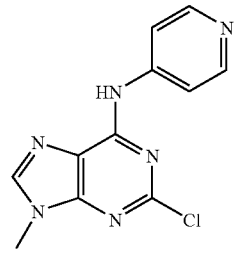 [SMILES: Cn1cnc2c(Nc3ccncc3)nc(Cl)nc21]

Was prepared according to Example 3 from N-pyridin-4-yl-formamide and 2,6-dichloro-9-methyl-9H-purine.

(2-Chloro-9-methyl-9H-purin-6-yl)-(5-chloro-pyridin-2-yl)-amine

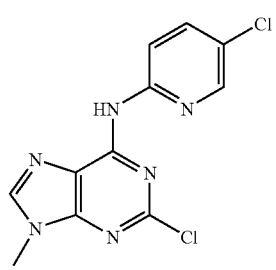 [SMILES: Cn1cnc2c(Nc3ccc(Cl)cn3)nc(Cl)nc21]

Was prepared according to Example 3 from N-(5-chloro-pyridin-2-yl)-formamide and 2,6-dichloro-9-methyl-9H-purine.

(2-Chloro-9-methyl-9H-purin-6-yl)-(6-chloro-pyridin-3-yl)-amine

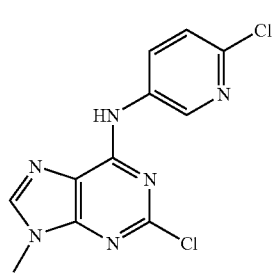 [SMILES: Cn1cnc2c(Nc3ccc(Cl)nc3)nc(Cl)nc21]

Was prepared according to Example 3 from N-(6-chloro-pyridin-3-yl)-formamide and 2,6-dichloro-9-methyl-9H-purine.

(2-Chloro-9-methyl-9H-purin-6-yl)-(4-nitro-phenyl)-amine

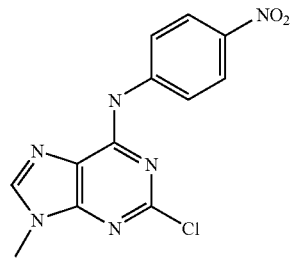 [SMILES: Cn1cnc2c(Nc3ccc([N+](=O)[O-])cc3)nc(Cl)nc21]

Was prepared according to Example 3 from N-(4-nitro-phenyl)-formamide and 2,6-dichloro-9-methyl-9H-purine.

4-(2-Chloro-9-methyl-9H-purin-6-ylamino)-benzonitrile

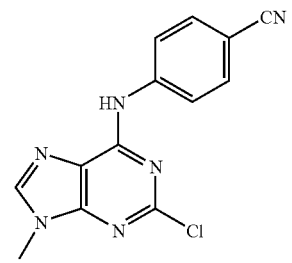 [SMILES: Cn1cnc2c(Nc3ccc(C#N)cc3)nc(Cl)nc21]

Was prepared according to Example 3 from N-(4-cyano-phenyl)-formamide and 2,6-dichloro-9-methyl-9H-purine.

(2-Chloro-9-methyl-9H-purin-6-yl)-phenyl-amine

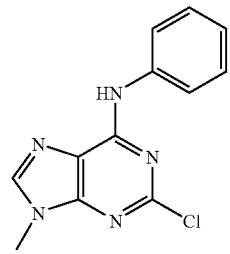 [SMILES: Cn1cnc2c(Nc3ccccc3)nc(Cl)nc21]

Was prepared according to Example 3 from N-phenyl-formamide and 2,6-dichloro-9-methyl-9H-purine.

(4-Bromo-phenyl)-(2-chloro-9-methyl-9H-purin-6-yl)-amine

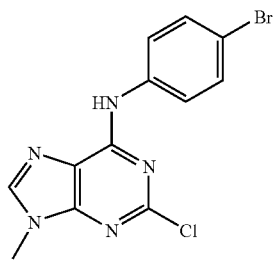 [SMILES: Cn1cnc2c(Nc3ccc(Br)cc3)nc(Cl)nc21]

Was prepared according to Example 3 from N-(4-bromo-phenyl)-acetamide and 2,6-dichloro-9-methyl-9H-purine.

(9-Benzyl-2-chloro-9H-purin-6-yl)-(4-chloro-phenyl)-amine and (7-benzyl-2-chloro-7H-purin-6-yl)-(4-chloro-phenyl)-amine

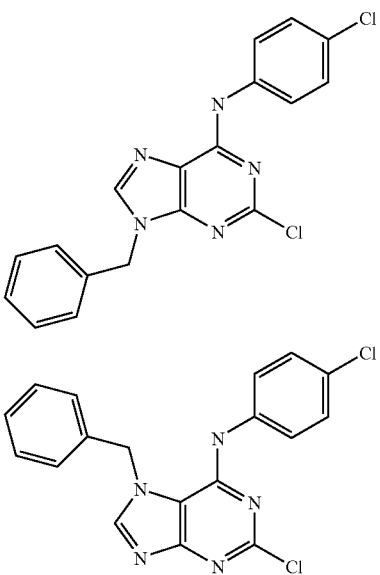

A mixture of (9-benzyl-2-chloro-9H-purin-6-yl)-(4-chloro-phenyl)-amine and (7-benzyl-2-chloro-7H-purin-6-yl)-(4-chloro-phenyl)-amine was prepared according Example 3 from a mixture of 9-benzyl-2,6-dichloro-9H-purine and 7-benzyl-2,6-dichloro-7H-purine and N-(4-chloro-phenyl)-formamide.

Example 4

(2-Chloro-9-methyl-9H-purin-6-yl)-cyclohexyl-amine

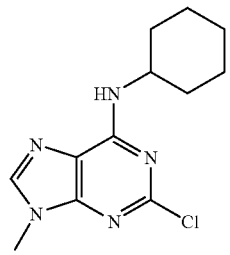 [SMILES: Cn1cnc2c(NC3CCCCC3)nc(Cl)nc21]

2,6-Dichloro-9-methyl-9H-purine (1.40 g, 6.93 mmol) was dissolved in acetonitrile (25 mL). Triethylamine (4.81 mL, 34.5 mmol) and cyclohexylamine (0.79 mL, 6.90 mmol) were added and the reaction mixture was stirred at 50° C. over night. The reaction mixture was cooled to room temperature and concentrated in vacuo. Water was added followed by extraction with ethyl acetate. The combined organic phases were dried over magnesium sulphate, filtered and concentrated in vacuo to give (2-chloro-9-methyl-9H-purin-6-yl)-cyclohexyl-amine (1.5 g, 82%) as a crystalline compound.

(2-Chloro-7-methyl-7H-purin-6-yl)-cyclohexyl-amine

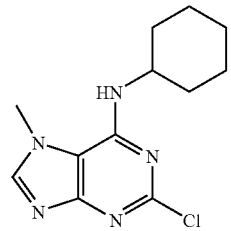 [SMILES: Cn1cnc2nc(Cl)nc(NC3CCCCC3)c21]

Was prepared according to Example 4 from 7-methyl-2,6-dichloro-7H-purine and cyclohexylamine.

(2-Chloro-9-methyl-9H-purin-6-yl)-phenethyl-amine

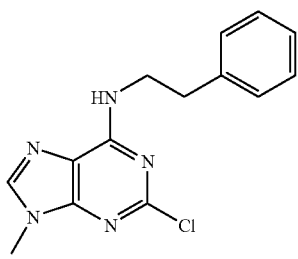 [SMILES: Cn1cnc2c(NCCc3ccccc3)nc(Cl)nc21]

Was prepared according to Example 4 from 9-methyl-2,6-dichloro-9H-purine and phenethylamine.

Example 5

(2-Chloro-9H-purin-6-yl)-cyclohexyl-amine

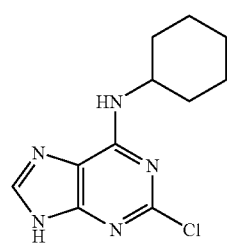 [SMILES: Clc1nc(NC2CCCCC2)c2nc[nH]c2n1]

2,6-Dichloropurine (2.5 g, 13.23 mmol) and cyclohexylamine (1.51 mL, 13.2 mmol) were dissolved in acetonitrile (25 mL) and heated to 50° C. for 5 days. The white precipitate was collected by filtration and used without further purification.

Example 6

(4-Chloro-phenyl)-[2-(3,5-dimethyl-pyrazol-1-yl)-9-methyl-9H-purin-6-yl]-amine (Compound 6.1)

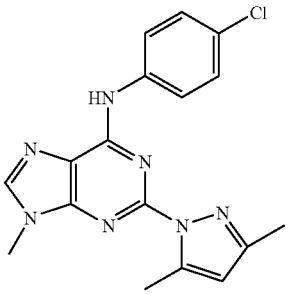 [SMILES: Cc1cc(C)n(-c2nc(Nc3ccc(Cl)cc3)c3ncn(C)c3n2)n1]

Sodium hydride (60% in mineral oil, 160 mg, 4.1 mmol) was added to 3,5-dimethylpyrazole (320 mg, 3.4 mmol) dissolved N,N-dimethylformamide (10 mL) and the mixture was stirred for 30 min. (2-Chloro-9-methyl-9H-purin-6-yl)-(4-chloro-phenyl)-amine (1.0 g 3.40 mmol) was added and the reaction mixture was heated at 120° C. for 4 days, cooled down and poured into water. The aqueous phase was extracted with ethyl acetate. The combined organic phases were dried over magnesium sulphate, filtered and concentrated in vacuo. The crude product was purified by flash chromatography (dichloromethane/methanol/ammonia) to give (4-chloro-phenyl)-[2-(3,5-dimethyl-pyrazol-1-yl)-9-methyl-9H-purin-6-yl]-amine (160 mg, 13%) as a yellow crystalline compound.

LC-ESI-HRMS of [M+H]+ shows 354.1227 Da. Calc. 354.123396 Da, dev. −2 ppm.

(4-Chloro-phenyl)-[2-(3,5-dimethyl-pyrazol-1-yl)-9-methyl-9H-purin-6-yl]-amine, sulfuric acid salt (4-Chloro-phenyl)-[2-(3,5-dimethyl-pyrazol-1-yl)-9-methyl-9H-purin-6-yl]-amine (10.0 g, 28.3 mmol) was dissolved in ethanol (200 mL). Sulfuric acid (1.7 mL, 31 mmol) was added drop-wise. The resulting white crystals were collected by filtration, washed with ethanol and dried to give (4-chloro-phenyl)-[2-(3,5-dimethyl-pyrazol-1-yl)-9-methyl-9H-purin-6-yl]-amine, sulforic acid salt (11.1 g, 87%) as a white crystalline compound. Mp. 218° C.

(4-Chloro-phenyl)-[2-(3,5-dimethyl-pyrazol-1-yl)-9-methyl-9H-purin-6-yl]-amine, hydrochloric acid salt (4-Chloro-phenyl)-[2-(3,5-dimethyl-pyrazol-1-yl)-9-methyl-9H-purin-6-yl]-amine (1.4 g, 4.0 mmol) was dissolved in ethanol (25 mL). Concentrated hydrochloric acid (0.4 mL, 4.3 mmol) was added drop-wise. The resulting white crystals were collected by filtration, washed with ethanol and dried to give (4-chloro-phenyl)-[2-(3,5-dimethyl-pyrazol-1-yl)-9-methyl-9H-purin-6-yl]-amine, hydrochloric acid salt (1.3 g, 84%) as a white crystalline compound.

(4-Chloro-phenyl)-[2-(3,5-dimethyl-pyrazol-1-yl)-9-methyl-9H-purin-6-yl]-amine, hydrobromic acid salt (4-Chloro-phenyl)-[2-(3,5-dimethyl-pyrazol-1-yl)-9-methyl-9H-purin-6-yl]-amine (500 mg, 1.4 mmol) was dissolved in ethanol (10 mL). Concentrated hydrobromic acid (0.12 mL, 1.6 mmol) was added drop-wise. The resulting white crystals were collected by filtration, washed with ethanol and dried to give (4-chloro-phenyl)-[2-(3,5-dimethyl-pyrazol-1-yl)-9-methyl-9H-purin-6-yl]-amine, hydrobroric acid salt (510 mg, 83%) as a white crystalline compound. Mp. 235° C.

Cyclohexyl-[2-(3,5-dimethyl-pyrazol-1-yl)-7-methyl-7H-purin-6-yl]-amine (Compound 6.2)

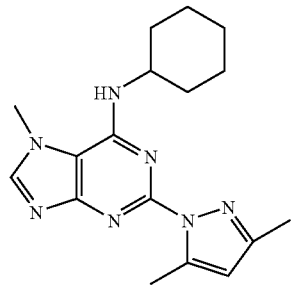 [SMILES: Cc1cc(C)n(-c2nc(NC3CCCCC3)c3c(ncn3C)n2)n1]

Was prepared according to Example 6 from (2-chloro-7-methyl-7H-purin-6-yl)-cyclohexyl-amine and 3,5-dimethylpyrazole.

LC-ESI-HRMS of [M+H]+ shows 326,2081 Da. Calc. 326,209318 Da, dev. −3.7 ppm.

(4-Chloro-phenyl)-[2-(3,5-dimethyl-pyrazol-1-yl)-7-methyl-7H-purin-6-yl]-amine (Compound 6.3)

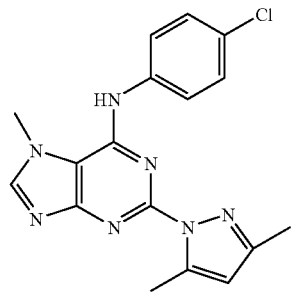 [SMILES: Cc1cc(C)n(-c2nc(Nc3ccc(Cl)cc3)c3c(ncn3C)n2)n1]

Was prepared according to Example 6 from (2-chloro-7-methyl-7H-purin-6-yl)-(4-chloro-phenyl)-amine and 3,5-dimethylpyrazole.

LC-ESI-HRMS of [M+H]+ shows 354,1226 Da. Calc. 354,123396 Da, dev. −2.2 ppm.

(4-Chloro-phenyl)-[2-(3,5-dimethyl-pyrazol-1-yl)-9-ethyl-9H-purin-6-yl]-amine (Compound 6.4)

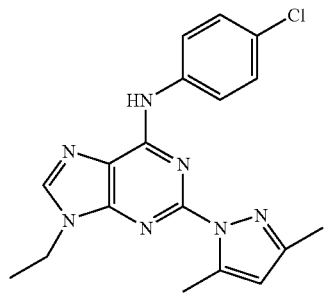 [SMILES: CCn1cnc2c(Nc3ccc(Cl)cc3)nc(-n3nc(C)cc3C)nc21]

Was prepared according to Example 6 from (2-chloro-9-ethyl-9H-purin-6-yl)-(4-chloro-phenyl)-amine and 3,5-dimethylpyrazole.

LC-ESI-HRMS of [M+H]+ shows 368,1399 Da. Calc. 368,139046 Da, dev. 2.3 ppm.

Benzo[1,3]dioxol-5-[2-(3,5-dimethyl-pyrazol-1-yl)-9-ethyl-9H-purin-6-yl]-amine (Compound 6.5)

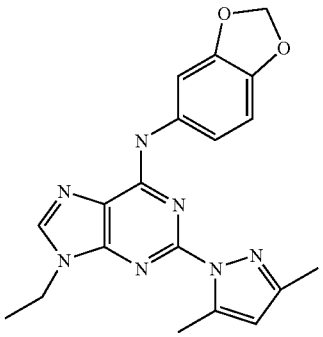 [SMILES: CCn1cnc2c(Nc3ccc4c(c3)OCO4)nc(-n3nc(C)cc3C)nc21]

Was prepared according to Example 6 from benzo[1,3]dioxol-5-yl-(2-chloro-9-ethyl-9H-purin-6-yl)-amine and 3,5-dimethylpyrazole.

LC-ESI-HRMS of [M+H]+ shows 378.1679 Da. Calc. 378.167848 Da, dev. 0.1 ppm.

6-(4-Chloro-phenylsulfanyl)-2-(3,5-dimethyl-pyrazol-1-yl)-9-methyl-9H-purine (Compound 6.6)

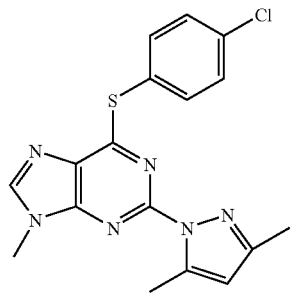 [SMILES: Cc1cc(C)n(-c2nc(Sc3ccc(Cl)cc3)c3ncn(C)c3n2)n1]

Was prepared according to Example 6 from 2-chloro-6-(4-chloro-phenyl-sulfanyl)-9-methyl-9H-purine and 3,5-dimethylpyrazole.

LC-ESI-HRMS of [M+H]+ shows 371.0863 Da. Calc. 371.084568 Da, dev. 4.7 ppm.

[2-(4-Chloro-3-methyl-pyrazol-1-yl)-9-methyl-9H-purin-6-yl]-(4-chloro-phenyl)-amine (Compound 6.7)

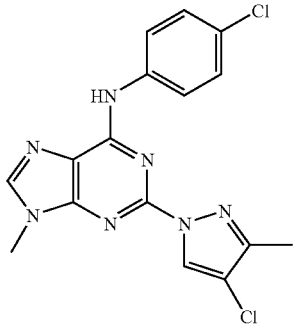 [SMILES: Cc1nn(-c2nc(Nc3ccc(Cl)cc3)c3ncn(C)c3n2)cc1Cl]

Was prepared according to Example 6 from (2-chloro-9-methyl-9H-purin-6-yl)-(4-chloro-phenyl)-amine and 4-chloro-3-methyl-1H-pyrazole.

LC-ESI-HRMS of [M+H]+ shows 374.0692 Da. Calc. 374.068774 Da, dev. 1.1 ppm.

[2-(5-Chloro-3-methyl-pyrazol-1-yl)-9-methyl-9H-purin-6-yl]-(4-chloro-phenyl)-amine (Compound 6.8)

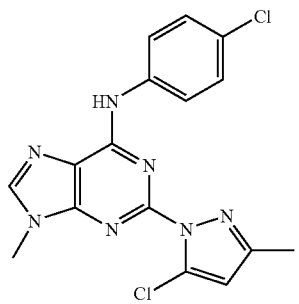 [SMILES: Cc1cc(Cl)n(-c2nc(Nc3ccc(Cl)cc3)c3ncn(C)c3n2)n1]

Was prepared according to Example 6 from (2-chloro-9-methyl-9H-purin-6-yl)-(4-chloro-phenyl)-amine and 5-chloro-3-methyl-1H-pyrazole.

LC-ESI-HRMS of [M+H]+ shows 374.0699 Da. Calc. 374.068774 Da, dev. 3 ppm.

Example 7

Cyclohexyl-[2-(3,5-dimethyl-pyrazol-1-yl)-9H-purin-6-yl]-amine (Compound 7.1)

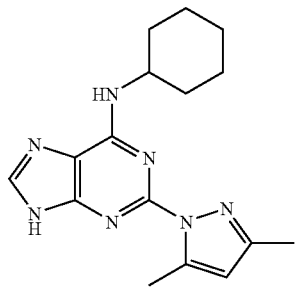 [SMILES: Cc1cc(C)n(-c2nc(NC3CCCCC3)c3nc[nH]c3n2)n1]

(2-Chloro-9H-purin-6-yl)-cyclohexyl-amine (1.0 g, 3.47 mmol), 3,5-dimethylpyrazole (834 mg, 8.68 mmol) and acetonitrile (10 mL) were mixed in a sealed vial and heated in a microwave oven at 200° C. for 50 min. Water was added and the precipitate was collected by filtration. The crude product was purified by flash chromatography (dichloromethane/methanol) to give cyclohexyl-[2-(3,5-dimethyl-pyrazol-1-yl)-9H-purin-6-yl]-amine (210 mg, 19%) as a white powder.

LC-ESI-HRMS of [M+H]+ shows 312.192 Da. Calc. 312.193668 Da, dev. −5.3 ppm.

Example 8

(4-Chloro-phenyl)-(2-hydrazino-9-methyl-9H-purin-6-yl)-amine

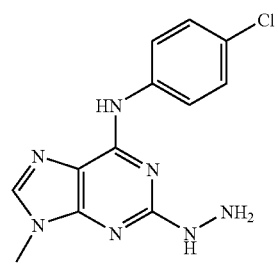 [SMILES: Cn1cnc2c(Nc3ccc(Cl)cc3)nc(NN)nc21]

(2-Chloro-9-methyl-9H-purin-6-yl)-(4-chloro-phenyl)-amine (3.58 g, 12.1 mmol) was dissolved in tetrahydrofuran (50 mL). Hydrazine monohydrate (26 mL, 536 mmol) was added and the reaction mixture was heated to reflux over night. The next day water was added and the resulting solid was collected by filtration, washed with water and dried to give (4-chloro-phenyl)-(2-hydrazino-9-methyl-9H-purin-6-yl)-amine (3.16 g, 90%) as a white crystalline compound.

(4-Chloro-phenyl)-(2-hydrazino-9-isobutyl-9H-purin-6-yl)-amine

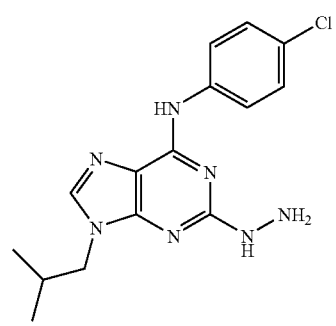 [SMILES: CC(C)Cn1cnc2c(Nc3ccc(Cl)cc3)nc(NN)nc21]

Was prepared according to Example 8 from (2-chloro-9-isobutyl-9H-purin-6-yl)-(4-chloro-phenyl)-amine and hydrazine monohydrate.

(4-Chloro-phenyl)-[9-(2-ethoxy-ethyl)-2-hydrazino-9H-purin-6-yl]-amine

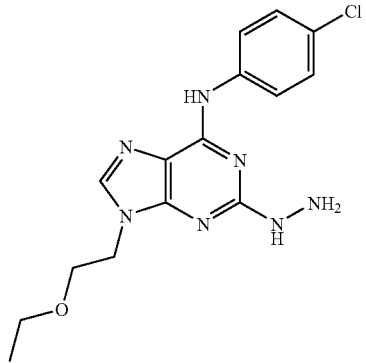 [SMILES: CCOCCn1cnc2c(Nc3ccc(Cl)cc3)nc(NN)nc21]

Was prepared according to Example 8 from [2-chloro-9-(2-ethoxy-ethyl)-9H-purin-6-yl]-(4-chloro-phenyl)-amine and hydrazine monohydrate.

(4-Fluoro-phenyl)-(2-hydrazino-9-methyl-9H-purin-6-yl)-amine

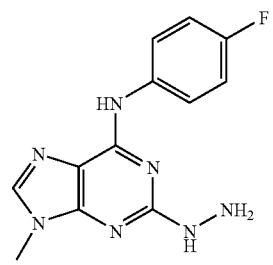 [SMILES: Cn1cnc2c(Nc3ccc(F)cc3)nc(NN)nc21]

Was prepared according to Example 8 from (2-chloro-9-methyl-9H-purin-6-yl)-(4-fluoro-phenyl)-amine and hydrazine monohydrate.

35

(2-Hydrazino-9-methyl-9H-purin-6-yl)-(4-trifluoromethyl-phenyl)-amine

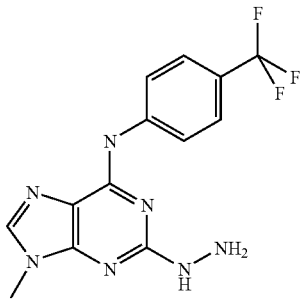 [SMILES: Cn1cnc2c(Nc3ccc(C(F)(F)F)cc3)nc(NN)nc21]

Was prepared according to Example 8 from (2-chloro-9-methyl-9H-purin-6-yl)-(4-trifluoromethyl-phenyl)-amine and hydrazine monohydrate.

(2-Hydrazino-9-methyl-9H-purin-6-yl)-pyridin-4-yl-amine

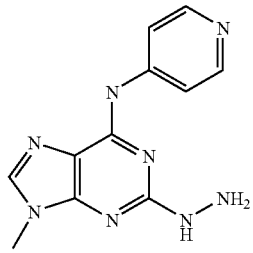 [SMILES: Cn1cnc2c(Nc3ccncc3)nc(NN)nc21]

Was prepared according to Example 8 from (2-chloro-9-methyl-9H-purin-6-yl)-pyridin-4-yl-amine and hydrazine monohydrate.

(5-Chloro-pyridin-2-yl)-(2-hydrazino-9-methyl-9H-purin-6-yl)-amine

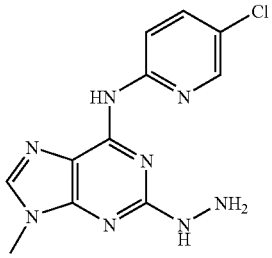 [SMILES: Cn1cnc2c(Nc3ccc(Cl)cn3)nc(NN)nc21]

Was prepared according to Example 8 from (2-chloro-9-methyl-9H-purin-6-yl)-(5-chloro-pyridin-2-yl)-amine and hydrazine monohydrate.

36

(6-Chloro-pyridin-3-yl)-(2-hydrazino-9-methyl-9H-purin-6-yl)-amine

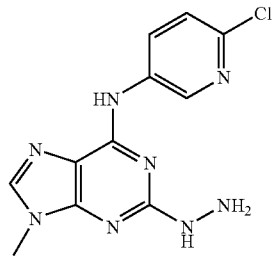 [SMILES: Cn1cnc2c(Nc3ccc(Cl)nc3)nc(NN)nc21]

Was prepared according to Example 8 from (2-chloro-9-methyl-9H-purin-6-yl)-(6-chloro-pyridin-3-yl)-amine and hydrazine monohydrate.

(2-Hydrazino-9-methyl-9H-purin-6-yl)-(4-nitro-phenyl)-amine

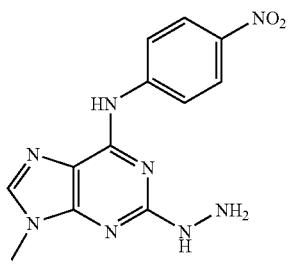 [SMILES: Cn1cnc2c(Nc3ccc([N+](=O)[O-])cc3)nc(NN)nc21]

Was prepared according to Example 8 from (2-chloro-9-methyl-9H-purin-6-yl)-(4-nitro-phenyl)-amine and hydrazine monohydrate.

4-(2-Hydrazino-9-methyl-9H-purin-6-ylamino)-benzonitrile

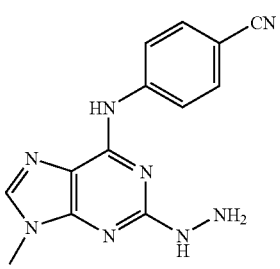 [SMILES: Cn1cnc2c(Nc3ccc(C#N)cc3)nc(NN)nc21]

Was prepared according to Example 8 from 4-(2-chloro-9-methyl-9H-purin-6-ylamino)-benzonitrile and hydrazine monohydrate.

37

(2-Hydrazino-9-methyl-9H-purin-6-yl)-phenyl-amine

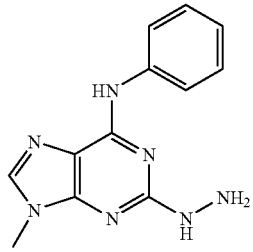 [SMILES: Cn1cnc2c(Nc3ccccc3)nc(NN)nc21]

Was prepared according to Example 8 from (2-chloro-9-methyl-9H-purin-6-yl)-phenyl-amine and hydrazine monohydrate.

(2-Hydrazino-9-methyl-9H-purin-6-yl)-phenethyl-amine

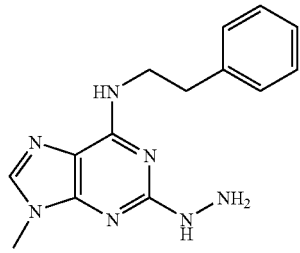 [SMILES: Cn1cnc2c(NCCc3ccccc3)nc(NN)nc21]

Was prepared according to Example 8 from (2-chloro-9-methyl-9H-purin-6-yl)-phenethyl-amine and hydrazine monohydrate.

(4-Bromo-phenyl)-(2-hydrazino-9-methyl-9H-purin-6-yl)-amine

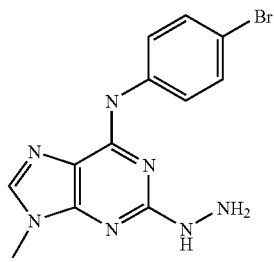 [SMILES: Cn1cnc2c(Nc3ccc(Br)cc3)nc(NN)nc21]

Was prepared according to Example 8 from (4-bromo-phenyl)-(2-chloro-9-methyl-9H-purin-6-yl)-amine and hydrazine monohydrate.

38

(9-Benzyl-2-hydrazino-9H-purin-6-yl)-(4-chloro-phenyl)-amine and (7-benzyl-2-hydrazino-7H-purin-6-yl)-(4-chloro-phenyl)-amine

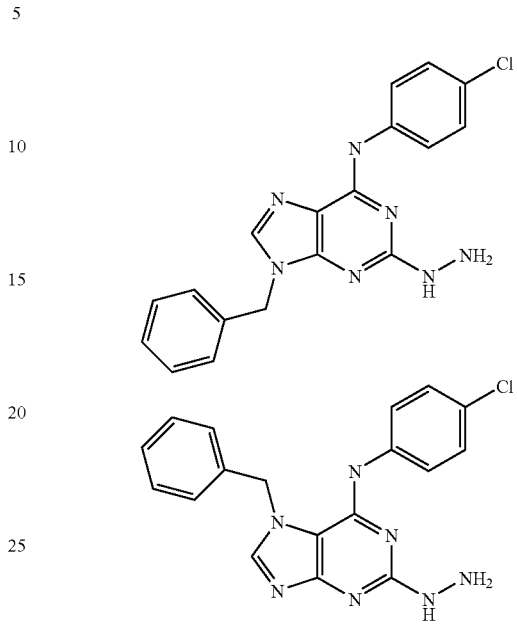

A mixture of (9-benzyl-2-hydrazino-9H-purin-6-yl)-(4-chloro-phenyl)-amine and (7-benzyl-2-hydrazino-7H-purin-6-yl)-(4-chloro-phenyl)-amine was prepared according to Example 8 from a mixture of (9-benzyl-2-chloro-9H-purin-6-yl)-(4-chloro-phenyl)-amine and (7-benzyl-2-chloro-7H-purin-6-yl)-(4-chloro-phenyl)-amine and hydrazine monohydrate.

Example 9

[2-(3,5-Dimethyl-pyrazol-1-yl)-9-methyl-9H-purin-6-yl]-(4-fluoro-phenyl)-amine (Compound 9.1)

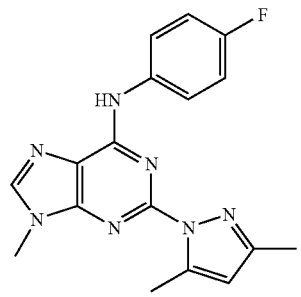 [SMILES: Cc1cc(C)n(-c2nc(Nc3ccc(F)cc3)c3ncn(C)c3n2)n1]

(4-Fluoro-phenyl)-(2-hydrazino-9-methyl-9H-purin-6-yl)-amine (900 mg, 3.29 mmol) and 2,4-pentanedione (0.47 mL, 4.16 mmol) in ethanol (25 mL) were heated to reflux for 20 min. Water was added and the white crystalline compound was collected by filtration, washed with water and dried to give [2-(3,5-dimethyl-pyrazol-1-yl)-9-methyl-9H-purin-6-yl]-(4-fluoro-phenyl)-amine (1.1 g, 100%).

LC-ESI-HRMS of [M+H]+ shows 338.1526 Da. Calc. 338.152946 Da, dev. −1 ppm.

(4-Chloro-phenyl)-[2-(3,5-dimethyl-pyrazol-1-yl)-9-isobutyl-9H-purin-6-yl]-amine (Compound 9.2)

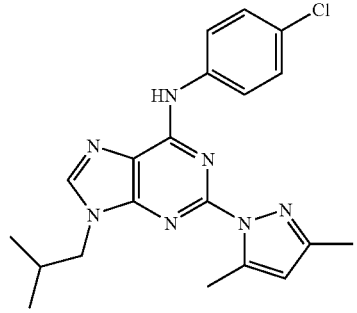 [SMILES: Cc1cc(C)n(-c2nc(Nc3ccc(Cl)cc3)c3ncn(CC(C)C)c3n2)n1]

Was prepared according to Example 9 from (4-chloro-phenyl)-(2-hydrazino-9-isobutyl-9H-purin-6-yl)-amine and 2,4-pentanedione.

(4-Chloro-phenyl)-[2-(3,5-dimethyl-pyrazol-1-yl)-9-(2-ethoxy-ethyl)-9H-purin-6-yl]-amine (Compound 9.3)

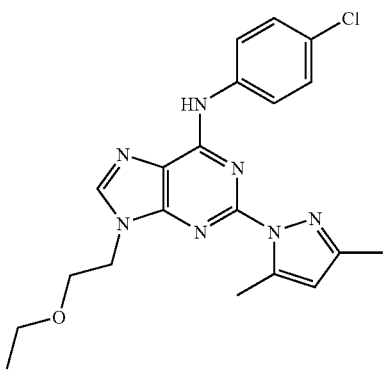 [SMILES: CCOCCn1cnc2c(Nc3ccc(Cl)cc3)nc(-n3nc(C)cc3C)nc21]

Was prepared according to Example 9 from (4-chloro-phenyl)-[9-(2-ethoxy-ethyl)-2-hydrazino-9H-purin-6-yl]-amine and 2,4-pentanedione.

[2-(3,5-Dimethyl-pyrazol-1-yl)-9-methyl-9H-purin-6-yl]-(4-trifluoromethyl-phenyl)-amine (Compound 9.4)

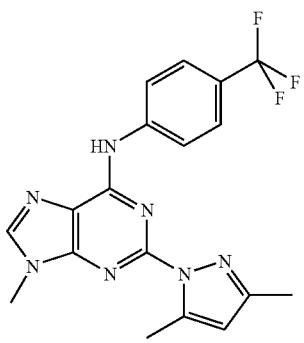 [SMILES: Cc1cc(C)n(-c2nc(Nc3ccc(C(F)(F)F)cc3)c3ncn(C)c3n2)n1]

Was prepared according to Example 9 from (2-hydrazino-9-methyl-9H-purin-6-yl)-(4-trifluoromethyl-phenyl)-amine and 2,4-pentanedione.

LC-ESI-HRMS of [M+H]+ shows 388.1517 Da. Calc. 388.149752 Da, dev. 5 ppm.

[2-(3,5-Dimethyl-pyrazol-1-yl)-9-methyl-9H-purin-6-yl]-pyridin-4-yl-amine (Compound 9.5)

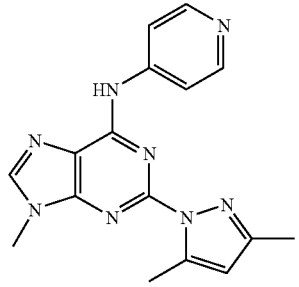 [SMILES: Cc1cc(C)n(-c2nc(Nc3ccncc3)c3ncn(C)c3n2)n1]

Was prepared according to Example 9 from (2-hydrazino-9-methyl-9H-purin-6-yl)-pyridin-4-yl-amine and 2,4-pentanedione.

LC-ESI-HRMS of [M+H]+ shows 321.1592 Da. Calc. 321.157617 Da, dev. 4.9 ppm.

(5-Chloro-pyridin-2-yl)-[2-(3,5-dimethyl-pyrazol-1-yl)-9-methyl-9H-purin-6-yl]-amine (Compound 9.6)

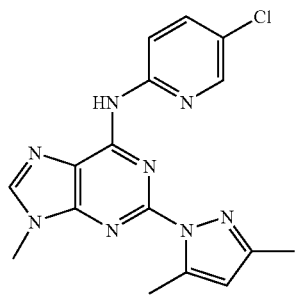 [SMILES: Cc1cc(C)n(-c2nc(Nc3ccc(Cl)cn3)c3ncn(C)c3n2)n1]

Was prepared according to Example 9 from (5-chloro-pyridin-2-yl)-(2-hydrazino-9-methyl-9H-purin-6-yl)-amine and 2,4-pentanedione.

LC-ESI-HRMS of [M+H]+ shows 355.1204 Da. Calc. 355.118645 Da, dev. 4.9 ppm.

(6-Chloro-pyridin-3-yl)-[2-(3,5-dimethyl-pyrazol-1-yl)-9-methyl-9H-purin-6-yl]-amine (Compound 9.7)

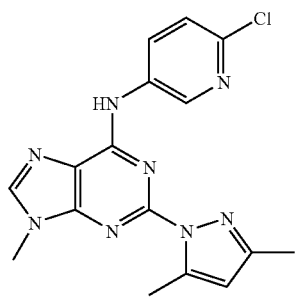

Was prepared according to Example 9 from (6-chloro-pyridin-3-yl)-(2-hydrazino-9-methyl-9H-purin-6-yl)-amine and 2,4-pentanedione.

LC-ESI-HRMS of [M+H]+ shows 355.1179 Da. Calc. 355.118645 Da, dev. −2.1 ppm

[2-(3,5-Dimethyl-pyrazol-1-yl)-9-methyl-9H-purin-6-yl]-(4-nitro-phenyl)-amine (Compound 9.8)

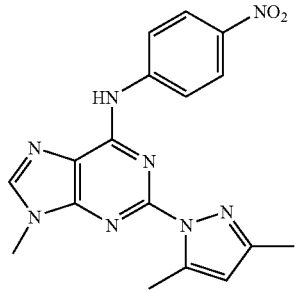 [SMILES: Cc1cc(C)n(-c2nc(Nc3ccc([N+](=O)[O-])cc3)c3ncn(C)c3n2)n1]

Was prepared according to Example 9 from (2-hydrazino-9-methyl-9H-purin-6-yl)-(4-nitro-phenyl)-amine and 2,4-pentanedione.
LC-ESI-HRMS of [M+H]+ shows 365.1461 Da. Calc. 365.147447 Da, dev. −3.7 ppm.

4-[2-(3,5-Dimethyl-pyrazol-1-yl)-9-methyl-9H-purin-6-ylamino]-benzonitrile (Compound 9.9)

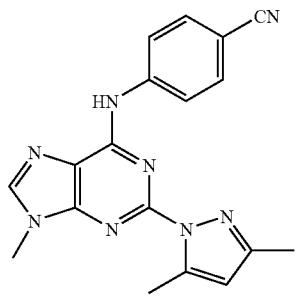 [SMILES: Cc1cc(C)n(-c2nc(Nc3ccc(C#N)cc3)c3ncn(C)c3n2)n1]

Was prepared according to Example 9 from 4-(2-hydrazino-9-methyl-9H-purin-6-ylamino)-benzonitrile and 2,4-pentanedione.
LC-ESI-HRMS of [M+H]+ shows 345.1593 Da. Calc. 345.157617 Da, dev. 4.9 ppm.

[2-(3,5-Dimethyl-pyrazol-1-yl)-9-methyl-9H-purin-6-yl]-phenyl-amine (Compound 9.10)

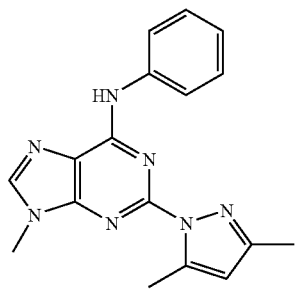 [SMILES: Cc1cc(C)n(-c2nc(Nc3ccccc3)c3ncn(C)c3n2)n1]

Was prepared according to Example 9 from (2-hydrazino-9-methyl-9H-purin-6-yl)-phenyl-amine and 2,4-pentanedione.
LC-ESI-HRMS of [M+H]+ shows 320.1629 Da. Calc. 320.162368 Da, dev. 1.7 ppm.

[2-(3,5-Dimethyl-pyrazol-1-yl)-9-methyl-9H-purin-6-yl]-phenethyl-amine (Compound

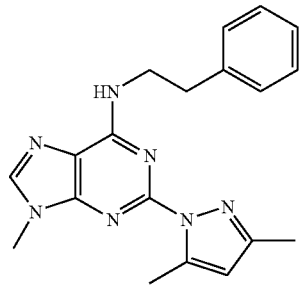 [SMILES: Cc1cc(C)n(-c2nc(NCCc3ccccc3)c3ncn(C)c3n2)n1]

Was prepared according to Example 9 from (2-hydrazino-9-methyl-9H-purin-6-yl)-phenethyl-amine and 2,4-pentanedione.
LC-ESI-HRMS of [M+H]+ shows 348.1941 Da. Calc. 348.193668 Da, dev. 1.2 ppm.

(4-Bromo-phenyl)-[2-(3,5-dimethyl-pyrazol-1-yl)-9-methyl-9H-purin-6-yl]-amine (Compound 9.12)

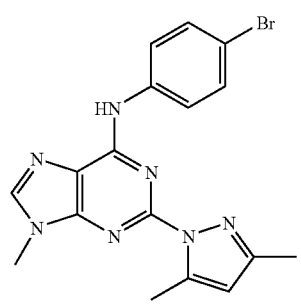 [SMILES: Cc1cc(C)n(-c2nc(Nc3ccc(Br)cc3)c3ncn(C)c3n2)n1]

Was prepared according to Example 9 from (4-bromo-phenyl)-(2-hydrazino-9-methyl-9H-purin-6-yl)-amine and 2,4-pentanedione.

(4-Chloro-phenyl)-[9-methyl-2-(5-methyl-3-trifluoromethyl-pyrazol-1-yl)-9H-purin-6-yl]-amine (Compound 9.13)

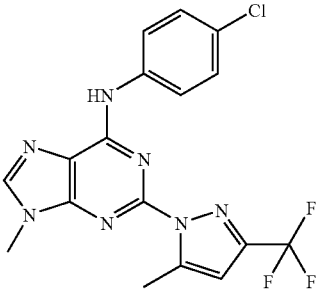 [SMILES: Cc1cc(C(F)(F)F)nn1-c1nc(Nc2ccc(Cl)cc2)c2ncn(C)c2n1]

Was prepared according to Example 9 from (4-chloro-phenyl)-(2-hydrazino-9-methyl-9H-purin-6-yl)-amine and 1,1,1-trifluoro-2,4-pentanedione.
LC-ESI-HRMS of [M+H]+ shows 408.0948 Da. Calc. 408.09513 Da, dev. −0.8 ppm (4-Chloro-phenyl)-[2-(3,5-diethyl-pyrazol-1-yl)-9-methyl-9H-purin-6-yl]-amine (Compound 9.14)

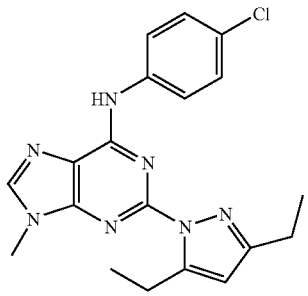 [SMILES: CCc1cc(CC)n(-c2nc(Nc3ccc(Cl)cc3)c3ncn(C)c3n2)n1]

Was prepared according to Example 9 from (4-chloro-phenyl)-(2-hydrazino-9-methyl-9H-purin-6-yl)-amine and 3,5-heptanedione.
LC-ESI-HRMS of [M+H]+ shows 382.1542 Da. Calc. 382.154696 Da, dev. −1.3 ppm.

(4-Chloro-phenyl)-[9-methyl-2-(3,4,5-trimethyl-pyrazol-1-yl)-9H-purin-6-yl]-amine (Compound 9.15)

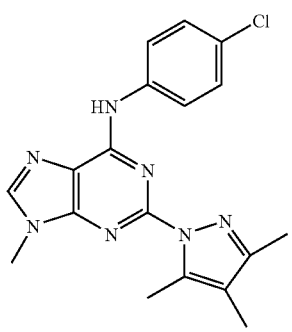 [SMILES: Cc1nn(-c2nc(Nc3ccc(Cl)cc3)c3ncn(C)c3n2)c(C)c1C]

Was prepared according to Example 9 from (4-chloro-phenyl)-(2-hydrazino-9-methyl-9H-purin-6-yl)-amine and 3-methyl-2,4-pentanedione.
LC-ESI-HRMS of [M+H]+ shows 368.1389 Da. Calc. 368.139046 Da, dev. −0.4 ppm.

[2-(4-Chloro-3,5-dimethyl-pyrazol-1-yl)-9-methyl-9H-purin-6-yl]-(4-chloro-phenyl)-amine (Compound 9.16)

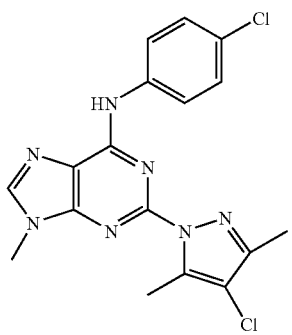 [SMILES: Cc1nn(-c2nc(Nc3ccc(Cl)cc3)c3ncn(C)c3n2)c(C)c1Cl]

Was prepared according to Example 9 from (4-chloro-phenyl)-(2-hydrazino-9-methyl-9H-purin-6-yl)-amine and 3-chloroacetylacetone.
LC-ESI-HRMS of [M+H]+ shows 388.0852 Da. Calc. 388.084424 Da, dev. 2 ppm.

(4-Chloro-phenyl)-[9-methyl-2-(5-methyl-3-phenyl-pyrazol-1-yl)-9H-purin-6-yl]-amine (Compound 9.17)

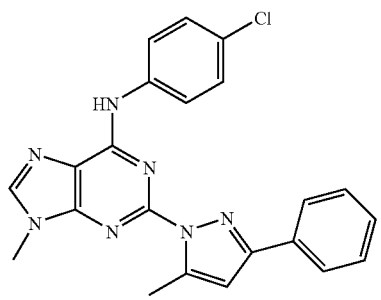 [SMILES: Cc1cc(-c2ccccc2)nn1-c1nc(Nc2ccc(Cl)cc2)c2ncn(C)c2n1]

Was prepared according to Example 9 from (4-chloro-phenyl)-(2-hydrazino-9-methyl-9H-purin-6-yl)-amine and benzoylacetone.
LC-ESI-HRMS of [M+H]+ shows 416.1393 Da. Calc. 416.139046 Da, dev. 0.6 ppm.

(4-Chloro-phenyl)-[2-(3-furan-2-yl-5-methyl-pyrazol-1-yl)-9-methyl-9H-purin-6-yl]-amine (Compound 9.18)

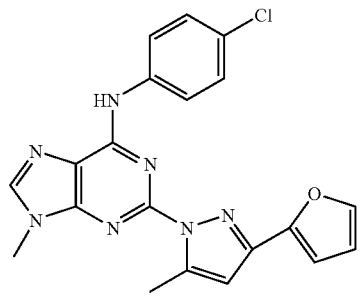 [SMILES: Cc1cc(-c2ccco2)nn1-c1nc(Nc2ccc(Cl)cc2)c2ncn(C)c2n1]

Was prepared according to Example 9 from (4-chloro-phenyl)-(2-hydrazino-9-methyl-9H-purin-6-yl)-amine and 1-(2-furyl)-1,3-butanedione.
LC-ESI-HRMS of [M+H]+ shows 406.1169 Da. Calc. 406.118311 Da, dev. −3.5 ppm.

1-[6-(4-Chloro-phenylamino)-9-methyl-9H-purin-2-yl]-5-methyl-1H-pyrazole-3-carboxylic acid ethyl ester (Compound 9.19)

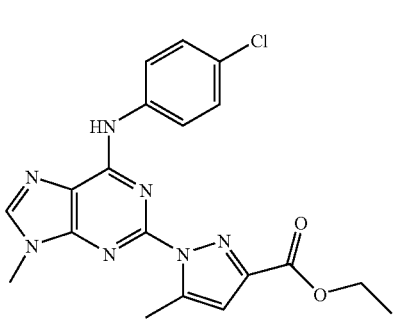 [SMILES: CCOC(=O)c1cc(C)n(-c2nc(Nc3ccc(Cl)cc3)c3ncn(C)c3n2)n1]

Was prepared according to Example 9 from (4-chloro-phenyl)-(2-hydrazino-9-methyl-9H-purin-6-yl)-amine and ethyl acetopyruvate.
LC-ESI-HRMS of [M+H]+ shows 412.1308 Da. Calc. 412.128876 Da, dev. 4.7 ppm.

[9-Benzyl-2-(3,5-dimethyl-pyrazol-1-yl)-9H-purin-6-yl]-(4-chloro-phenyl)-amine and [7-benzyl-2-(3,5-dimethyl-pyrazol-1-yl)-7H-purin-6-yl]-(4-chloro-phenyl)-amine

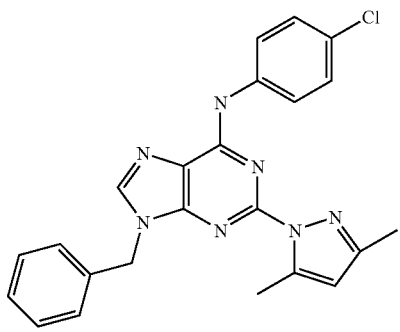

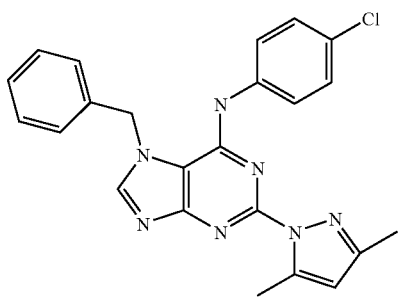

A mixture of [9-benzyl-2-(3,5-dimethyl-pyrazol-1-yl)-9H-purin-6-yl]-(4-chloro-phenyl)-amine and [7-benzyl-2-(3,5-dimethyl-pyrazol-1-yl)-7H-purin-6-yl]-(4-chloro-phenyl)-amine was prepared according to Example 9 from (9-benzyl-2-hydrazino-9H-purin-6-yl)-(4-chloro-phenyl)-amine and (7-benzyl-2-hydrazino-7H-purin-6-yl)-(4-chloro-phenyl)-amine and 2,4-pentanedione.

3-{[6-(4-Chloro-phenylamino)-9-methyl-9H-purin-2-yl]-hydrazono}-1,1,1,4,4,4-hexafluoro-butan-2-one

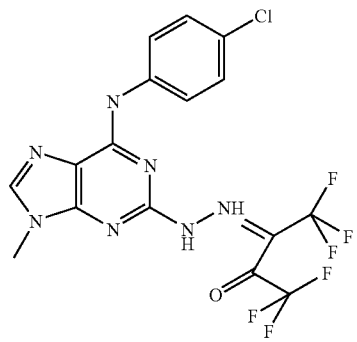 [SMILES: Cn1cnc2c(Nc3ccc(Cl)cc3)nc(N/N=C(\C(=O)C(F)(F)F)C(F)(F)F)nc21]

Was prepared according to Example 9 from (4-chloro-phenyl)-(2-hydrazino-9-methyl-9H-purin-6-yl)-amine and hexafluoroacetylacetone.

Example 10

[2-(3,5-Bis-trifluoromethyl-pyrazol-1-yl)-9-methyl-9H-purin-6-yl]-(4-chloro-phenyl)-amine (Compound 10.1)

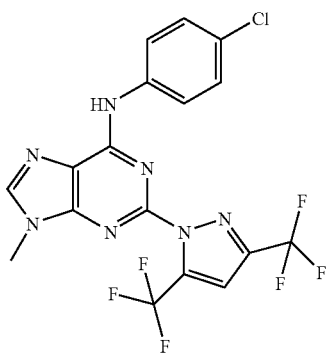 [SMILES: Cn1cnc2c(Nc3ccc(Cl)cc3)nc(-n3nc(C(F)(F)F)cc3C(F)(F)F)nc21]

Small pieces of sodium (200 mg 8.7 mmol) was added to methanol (40 mL) and stirred for 30 min. 3-{[6-(4-chloro-phenylamino)-9-methyl-9H-purin-2-yl]-hydrazono}-1,1,1,4,4,4-hexafluoro-butan-2-one (1.3 g, 2.7 mmol) was added and the reaction mixture was heated at reflux over night. Upon cooling a white solid precipitated. The crystals were collected by filtration and recrystallised from methanol to give [2-(3,5-bis-trifluoromethyl-pyrazol-1-yl)-9-methyl-9H-purin-6-yl]-(4-chloro-phenyl)-amine (460 mg, 37%) as white crystals.

LC-ESI-HRMS of [M+H]+ shows 462.0668 Da. Calc. 462.066864 Da, dev. −0.1 ppm.

Example 11

N-[2-(3,5-Dimethyl-pyrazol-1-yl)-9-methyl-9H-purin-6-yl]-benzene-1,4-diamine (Compound 11.1)

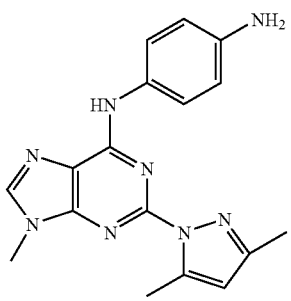 [SMILES: Cc1cc(C)n(-c2nc(Nc3ccc(N)cc3)c3ncn(C)c3n2)n1]

[2-(3,5-Dimethyl-pyrazol-1-yl)-9-methyl-9H-purin-6-yl]-(4-nitro-phenyl)-amine (2.89 g, 7.93 mmol) was dissolved in methanol (50 mL) and dichloromethane (50 mL). Palladium on carbon (5%, 600 mg) was added and the reaction mixture was stirred under a hydrogen atmosphere for 24 hours. Filtration through celite followed by concentration in vacuo gave N-[2-(3,5-dimethyl-pyrazol-1-yl)-9-methyl-9H-purin-6-yl]-benzene-1,4-diamine (2.6 g, 98%) as a yellow foam.

LC-ESI-HRMS of [M+H]+ shows 335.1733 Da. Calc. 335.173267 Da, dev. 0.1 ppm

Example 12

(4-Chloro-phenyl)-{9-methyl-2-[3-methyl-5-(tetrahydro-pyran-2-yloxymethyl)-pyrazol-1-yl]-9H-purin-6-yl}-amine

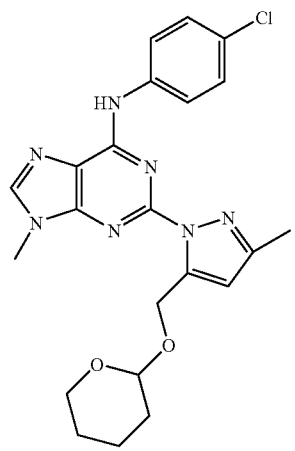 [SMILES: Cc1cc(COC2CCCCO2)n(-c2nc(Nc3ccc(Cl)cc3)c3ncn(C)c3n2)n1]

Under a nitrogen atmosphere tetrahydro-2-(2-propynyloxy)-2H-pyran (636 mL, 4.52 mmol) was dissolved in dry tetrahydrofuran (20 mL) and cooled to −78° C. n-Butyl-lithium (2.5 M in hexanes, 2.03 mL, 5.06 mmol) was added drop-wise. Zinc chloride (629 mg, 4.51 mmol) dissolved in tetrahydrofuran (5 mL) was added drop-wise and the reaction mixture was allowed to warm to 0° C. Acetyl chloride (0.35 mL, 4.93 mmol) was added followed by heating to 40° C. for 45 min. The reaction was quenched with saturated aqueous ammonium chloride. Ethyl acetate was added and the phases were separated. The organic phase was washed with saturated aqueous ammonium chloride (2×) and brine, dried over magnesium sulphate, filtered and concentrated in vacuo to give 4-(tetrahydro-pyran-2-yloxy)-but-3-yn-2-on as the crude product.

4-(Tetrahydro-pyran-2-yloxy)-but-3-yn-2-on (824 mg, 4.5 mmol) and (4-chloro-phenyl)-(2-hydrazino-9-methyl-9H-purin-6-yl)-amine (1.5 g, 5.2 mmol) were dissolved in ethanol (30 mL) and heated at reflux for 24 hours. The reaction mixture was concentrated in vacuo. The crude product was purified by flash chromatography (dichloromethane/methanol/ammonia) to give (4-chloro-phenyl)-{9-methyl-2-[3-methyl-5-(tetrahydro-pyran-2-yloxymethyl)-pyrazol-1-yl]-9H-purin-6-yl}-amine (240 mg, 12%) as an yellow foam.

Example 13

{2-[6-(4-Chloro-phenylamino)-9-methyl-9H-purin-2-yl]-5-methyl-2H-pyrazol-3-yl}-methanol (Compound 13.1)

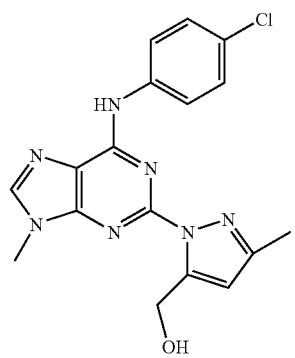 [SMILES: Cc1cc(CO)n(-c2nc(Nc3ccc(Cl)cc3)c3ncn(C)c3n2)n1]

(4-Chloro-phenyl)-{9-methyl-2-[3-methyl-5-(tetrahydro-pyran-2-yloxymethyl)-pyrazol-1-yl]-9H-purin-6-yl}-amine (240 mg, 0.53 mmol) was dissolved in methanol (30 mL). p-Toluenesulfonic acid monohydrate (90 mg, 0.48 mmol) was added and the reaction mixture was heated to reflux for 24 hours. Upon cooling a white crystalline compound was formed. The crystals were stirred with potassium carbonate (2 M), collected by filtration, washed with water and dried to give {2-[6-(4-chloro-phenyl-amino)-9-methyl-9H-purin-2-yl]-5-methyl-2H-pyrazol-3-yl}-methanol (60 mg, 31%)

LC-ESI-HRMS of [M+H]+ shows 370.1176 Da. Calc. 370.118311 Da, dev. −1.9 ppm

Example 14

[2-(3,5-Dimethyl-pyrazol-1-yl)-9H-purin-6-yl]-phenyl-amine (Compound 14.1)

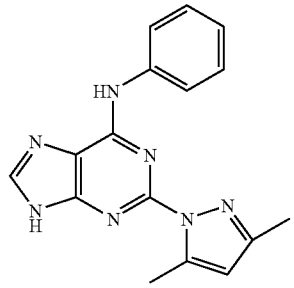 [SMILES: Cc1cc(C)n(-c2nc(Nc3ccccc3)c3nc[nH]c3n2)n1]

Ammonia (75 mL) was condensed in a reaction flask equipped with a mechanical stirrer and cooled on an acetone dry-ice bath. A mixture of [9-benzyl-2-(3,5-dimethyl-pyrazol-1-yl)-9H-purin-6-yl]-(4-chloro-phenyl)-amine and [7-benzyl-2-(3,5-dimethyl-pyrazol-1-yl)-7H-purin-6-yl]-(4-chloro-phenyl)-amine (1.5 g, 3.49 mmol) was added. Under vigorous stirring small pieces of sodium (2 equiv) were added. When the addition was completed the reaction mixture turned dark blue. The mixture was stirred for 2 minutes followed by careful addition of ammonium chloride. The reaction mixture was allowed to warm to room temperature. Water and a small amount of concentrated hydrochloric acid were added. The resulting solid was collected by filtration, washed with water and ether and dried to give [2-(3,5-dimethyl-pyrazol-1-yl)-9H-purin-6-yl]-phenyl-amine (590 mg, 50%) as a white solid.

LC-ESI-HRMS of [M+H]+ shows 306.1478 Da. Calc. 306.146718 Da, dev. 3.5 ppm.

Example 15

[2-(3,5-Dimethyl-pyrazol-1-yl)-9-(2-methoxy-ethyl)-9H-purin-6-yl]-phenyl-amine (Compound 15.1)

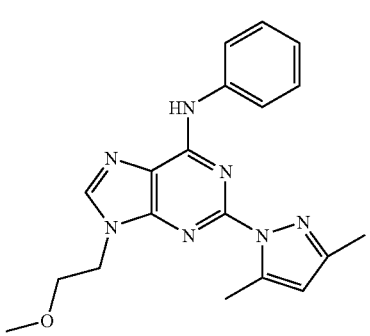

[2-(3,5-Dimethyl-pyrazol-1-yl)-9H-purin-6-yl]-phenyl-amine (300 mg, 0.88 mmol), 2-bromoethylmethylether (0.12 mL, 1.32 mmol), potassium carbonate (121 mg, 0.88 mmol) and acetonitrile were mixed and heated in a microwave oven at 120° C. for 40 min. Water was added resulting in a white precipitate. The crude product was purified by preparative LCMS to give [2-(3,5-dimethyl-pyrazol-1-yl)-9-(2-methoxy-ethyl)-9H-purin-6-yl]-phenyl-amine (27 mg, 9%) as a white crystalline compound.

LC-ESI-HRMS of [M+H]+ shows 364.1899 Da. Calc. 364.188583 Da, dev. 3.6 ppm.

Example 16

Biological Activity

This below example demonstrates the biological activity of the compounds of the invention. The ionic current through small-conductance $Ca^{2+}$-activated $K^+$ channels (SK channels, subtype 3) is recorded using the whole-cell configuration of the patch-clamp technique in a classic patch-clamp set-up using HEK293 tissue culture cells expressing hSK3 channels as described in e.g. WO 2006/100212.

The $SC_{100}$ value determined is defined as the Stimulating Concentration required for increasing the baseline current by 100%. The below $SC_{100}$ values are an indication of the SK3 activating properties of the compounds of the invention.

| Compound | The $SC_{100}$ (μM) |
|---|---|
| 6.1 | 0.02 |
| 6.4 | 0.01 |
| 9.1 | 0.05 |
| 9.7 | 0.4 |
| 9.8 | 0.2 |
| 9.11 | 0.2 |
| 9.14 | 0.6 |
| 9.16 | 0.02 |
| 9.18 | 1.0 |
| 13.1 | 0.2 |
| 14.1 | 0.2 |
| 15.1 | 0.4 |

The invention claimed is:

1. A purinyl derivative of Formula Ia or Ib

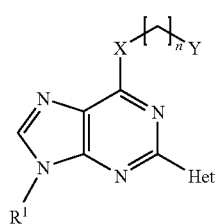
(Ia)

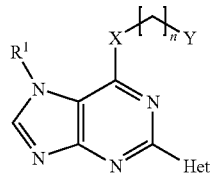
(Ib)

or a pharmaceutically acceptable salt thereof, wherein
n is 0;
X represents NH;
Y represents phenyl, optionally substituted with halo;
$R^1$ represents alkyl; and
Het represents a pyrazolyl group substituted two or more times with alkyl.

2. The purinyl derivative of claim 1, or a pharmaceutically acceptable salt thereof, wherein Y represents phenyl substituted with halo.

3. The purinyl derivative of claim 1, or a pharmaceutically acceptable salt thereof, wherein $R^1$ represents methyl.

4. The purinyl derivative according to claim 1, or a pharmaceutically acceptable salt thereof, wherein Het represents pyrazolyl which is substituted two times with alkyl.

5. The purinyl derivative of claim 1, which is
(4-Chloro-phenyl)-[2-(3,5-dimethyl-pyrazol-1-yl)-9-methyl-9H-purin-6-yl]-amine;
(4-Chloro-phenyl)-[2-(3,5-dimethyl-pyrazol-1-yl)-7-methyl-7H-purin-6-yl]-amine;
(4-Chloro-phenyl)-[2-(3,5-dimethyl-pyrazol-1-yl)-9-ethyl-9H-purin-6-yl]-amine;
[2-(3,5-Dimethyl-pyrazol-1-yl)-9-methyl-9H-purin-6-yl]-(4-fluoro-phenyl)-amine;
(4-Chloro-phenyl)-[2-(3,5-dimethyl-pyrazol-1-yl)-9-isobutyl-9H-purin-6-yl]-amine;
[2-(3,5-Dimethyl-pyrazol-1-yl)-9-methyl-9H-purin-6-yl]-phenyl-amine;
(4-Bromo-phenyl)-[2-(3,5-dimethyl-pyrazol-1-yl)-9-methyl-9H-purin-6-yl]-amine;
(4-Chloro-phenyl)-[2-(3,5-diethyl-pyrazol-1-yl)-9-methyl-9H-purin-6-yl]-amine;
(4-Chloro-phenyl)-[9-methyl-2-(3,4,5-trimethyl-pyrazol-1-yl)-9H-purin-6-yl]-amine;
or a pharmaceutically acceptable salt thereof.

6. A pharmaceutical composition comprising a therapeutically-effective amount of a purinyl derivative according to claim 1, or a pharmaceutically-acceptable addition salt thereof, or a prodrug thereof, together with at least one pharmaceutically-acceptable carrier or diluent.

7. The purinyl derivative of claim 1, which is
(4-Chloro-phenyl)-[2-(3,5-dimethyl-pyrazol-1-yl)-9-methyl-9H-purin-6-yl]-amine; or a pharmaceutically acceptable salt thereof.

* * * * *